US011609197B2

United States Patent
Lépinay et al.

(10) Patent No.: US 11,609,197 B2
(45) Date of Patent: Mar. 21, 2023

(54) SMOKE POINT AUTOMATIC CORRECTION

(71) Applicant: AD Systems S.A.S., Saint André sur Orne (FR)

(72) Inventors: Martial Lépinay, Mouen (FR); Jean Christien, Saint Martin de Fontenay (FR)

(73) Assignee: AD Systems S.A.S., Saint André sur Orne (FR)

( * ) Notice: Subject to any disclaimer, the term of this patent is extended or adjusted under 35 U.S.C. 154(b) by 122 days.

(21) Appl. No.: 17/343,251

(22) Filed: Jun. 9, 2021

(65) Prior Publication Data
US 2021/0404980 A1 Dec. 30, 2021

Related U.S. Application Data

(60) Provisional application No. 63/045,592, filed on Jun. 29, 2020.

(51) Int. Cl.
*G01N 25/52* (2006.01)
*G06T 7/60* (2017.01)

(52) U.S. Cl.
CPC ............... *G01N 25/52* (2013.01); *G06T 7/60* (2013.01)

(58) Field of Classification Search
CPC ........ G01N 25/52; G01N 33/28; G01N 21/72; G01N 21/274; G06T 7/60
See application file for complete search history.

(56) References Cited

U.S. PATENT DOCUMENTS

| 6,662,116 | B2 | 12/2003 | Brown | |
| 7,829,343 | B2 | 11/2010 | Reminiac et al. | |
| 2018/0209853 | A1* | 7/2018 | Kraus | .................... G01J 5/0014 |
| 2020/0364498 | A1* | 11/2020 | Trifol | ........................ F23G 7/05 |

OTHER PUBLICATIONS

Ombrello et al., "Burner platform for sub-atmospheric pressure flame studies", Combustion and Flame 159 (2012) 2363-2373 (Year: 2012).*

(Continued)

*Primary Examiner* — Qian Yang
(74) *Attorney, Agent, or Firm* — Vorys, Sater, Seymour and Pease LLP

(57) ABSTRACT

A testing device and method for determining smoke point of a hydrocarbon. The device including: an apparatus for determining the smoke point conforming to specifications of an ASTM D1322-19 standard or equivalent standard, imaging device for taking a series of digital images of a flame; ambient relative humidity sensor for measuring relative humidity; ambient temperature sensor for measuring temperature; computer system linked to the imaging device, humidity sensor, and temperature sensor programmed to analyze digital images from the imaging device to measure flame height flame, and use temperature with relative humidity measured by the temperature and humidity sensors to calculate absolute humidity and correct measured flame height as a function of difference between the calculated absolute humidity and normalized absolute humidity, and preferably to correct measured flame height as a function of difference between pressure during flame height measuring and normalized pressure.

13 Claims, 10 Drawing Sheets

(56) References Cited

OTHER PUBLICATIONS

Lillo et al., "Diesel Spray Ignition Detection and Spatial/Temporal Correction", SAE International Journal of Engines, vol. 5, No. 3 (Aug. 2012), pp. 1330-1346 (Year: 2012).*
Fu et al., "Study on laminar flame speed and flame structure of syngas with varied compositions using OH-PLIF and spectrograph", International Journal of Hydrogen Energy 38 (2013) 1636 -1643 (Year: 2013).*
Gaur et al., "Video Flame and Smoke Based Fire Detection Algorithms: A Literature Review", Fire Technology, 56, 1943-1980, 2020 (Year: 2020).*
McGrain et al., "Measurements of the soot vol. field in laminar diffusion flames at elevated pressures", Combustion and Flame 140 (2005) 60-69 (Year: 2005).*
Graziano Barbara, et al, Advanced Methodology for the Detection of Smoke Point Heights in Hydrocarbon Flames, Energy & Fuels, vol. 32, No. 3, Feb. 4, 2018, pp. 3908-3919, XP055840348, Washington, DC, US.
Rubio-Gomez Guilllermo, et al, "Vision based algorithm for automated determination of smoke point of diesel blends", Fuel, IPC Sience and Technology Press, Guildford, GB, vol. 235, Aug. 17, 2018 pp. 595-602, XP085500457, ISSN: 0016-2361.
Watson Roger J., et al, An improved methodology for determining threshold sooting indices from smoke point lamps, Fuel, IPC Sience and Technology Press, Guildford, GB, vol. 111, Apr. 28, 2013, pp. 120-130, XP028565511, ISSN: 0016-2361.
International Search Report and Written Opinion dated Sep. 22, 2021 for PCT/IB2021/055488 to AD Systems S.A.S. filed Jun. 22, 2021.
ASTM D1322-19, Standard Test Method for Smoke Point of Kerosene and Aviation Turbine Fuel, ASTM International, West Conshohocken, PA, 2019, www.astm.org, downloaded Jun. 26, 2020.
ASTM D1322-18, Standard Test Method for Smoke Point of Kerosene and Aviation Turbine Fuel, ASTM International, West Conshohocken, PA, 2019, www.astm.org, downloaded Jul. 25, 2018.
Etech SP01 User Manual, Aviation fuel smoke point tester user's Guide, Beijing Rundong Instrument Factory, Apr. 20, 2020.
EIE-SP-01, Jet Fuel Smoke Point Tester, etech@etech-eie.com, Apr. 17, 2020.
Smoke Point of Kerosene and Aviation Turbine Fuel, ASTM D1322, SP10—Automated Smoke Point, AD systems, Apr. 17, 2020.
Automated Smoke Point—SP10, Technical description & Ordering information, Automated Smoke Point—SP10 West methods: ASTM D1322, IP 598, Standard Specification for Aviation Turbine Fuel ASTM D1655, D7566 and Def Stan 91-91, pp. 1-8, AD Systems—Sep. 2015.

* cited by examiner

SMOKE POINT AUTOMATIC CORRECTION

FIELD OF THE INVENTION

The invention provides a method and apparatus for correcting measured smoke point to account for ambient humidity and temperature and optionally pressure.

BACKGROUND

The smoke point of a hydrocarbon is a characteristic that is routinely determined in refinery laboratories, for example, on kerosenes, aviation fuels, lamp oils, etc. This characteristic is an important parameter since it is directly linked to the hydrocarbon composition of the particular fuel being tested. In practice, the greater the Carbon (C) to Hydrogen (H) ratio (C:H) and, therefore the lower the aromatic compound content, the higher the smoke point becomes and the better the fuel behaves on its combustion. In other words, the smoke point is quantitatively linked to the potential transfer of radiative heat and, in as much as this heat transfer exerts a strong influence on the temperature of the metallic parts, the smoke point therefore becomes a predictive indicator of the longevity of said metallic parts.

A drawback of using the smoke point as a predictive indicator, however, is that it has been difficult to measure. Normally, a standardized analysis method is used to enable the detection (such as the method described in the ASTM D1322-19, Standard Test Method for Smoke Point of Kerosene and Aviation Turbine Fuel, ASTM International, West Conshohocken, Pa., 2019, www.astm.org incorporated herein by reference, and its equivalents, such as ISO 3014, IP 57 and NF M 07-028), and then a maximum flame height of the tested hydrocarbon sample without formation of smoke is measured. This measurement is typically expressed in millimeters ("mm") and accurate to the nearest tenth of a mm. There is no (or very little) difference between the ASTM D1322-19 standard and the ISO, IP, NF, GOST, HS, etc. standards.

In such a measurement, the hydrocarbon test sample is burned in a wick lamp having a candle and the wick (also described in the ASTM D1322-19 standard). The test involves setting the wick height and varying the position of the candle to gradually modify the height and the appearance of the flame in the following flame appearance sequence. The height and appearance of the flame changes slowly from a relatively elongated and jumpy state with a pointed tip with the sides of the tip appearing concave upward, in which a top end of the flame gives off a light smoke, to a state in which the flame height is shorter with a top end of the flame is perfectly well rounded. Between these two flame states, the test operator must also distinguish between two other intermediate flame shapes, namely an intermediate flame shape having an elongated point and edges that appear concave at its top part, and another intermediate flame shape in which the pointed end of the flame has just disappeared and where the flame is slightly rounded (slightly blunted) and without smoke. When the flame has this last appearance, the operator or automatic measuring device (using digital images) records the height of the flame on a scale graduated in mm positioned inside and at the back of the lamp. Make three separate observations of the flame height at the smoke point by repeating the flame appearance sequence a total of three successive measurements. If these measured values vary over a range greater than 1.0 mm, repeat the test with a fresh sample and another wick. The final value of the smoke point retained for the sample under analysis is the average of three successive measurements calculated to the nearest 0.1 mm.

Like all the analysis methods of this type, the manual method of measuring the smoke point, as defined in the ASTM D1322-19 standard, does, however, have limitations in terms of accuracy. For example, it is often difficult for the test operator to judge the correct appearance of the flame and to determine the correct moment at which the flame height should be measured on the graduated scale. To ensure quality results when measuring flame height, certain procedures and precautions should be implemented, but implementation of such procedures and precautions depends entirely on the test operator. Thus, the repeatability and reproducibility of the standardized test are respectively 2 mm and 3 mm.

U.S. Pat. No. 7,829,343 to Reminiac et al discloses an automated method and device for determining the smoke point of a hydrocarbon in accordance with the ASTM D1322 standard or equivalents thereof as an improvement to the manual method. U.S. Pat. No. 7,829,343 to Reminiac et al discloses a method and device for determining the smoke point of a hydrocarbon, comprising, among the different steps defined in the ASTM D1322 standard or equivalents thereof, the identification, among different aspects of the flame according to the position of the burner in the lamp, of a particular aspect of the flame and the reading of the height of this flame on a graduated scale in mm. It is characterized by the fact that a series of digital images of the flame is taken and recorded with the aid of a digital camera or the like at intervals sufficiently close for permitting, by analyzing these digital images, the detection of a sudden change in the shape of the flame, and that the height of this flame is measured at the moment of this sudden change in its shape. The height being considered as the smoke point of the tested hydrocarbon. A commercial device that employs this patented system is the AD Systems Automated Smoke Point-SP10. AD Systems Automated Smoke Point-SP10 uses a system that adjusts the size of the flame associated to a video camera that observes the flame. When the flame attains the shape described in the test method, the SP10 memorizes and reports the height of the flame. The SP10 has been made the referee method in ASTM D1322: Section 6.2.2 of ASTM D1322-19 states, "Due to the vastly superior resolution of the digital camera compared to the human eye, smoke point shall be measured by the automated unit when available. In case of dispute between results from manual and automated methods, the referee shall be considered the automated method."

However, smoke point measurements obtained via current systems and methods may be adversely impacted by ambient pressure conditions experienced or encountered at the test site. Thus, current systems are calibrated to account for barometric pressure.

According to Section 10 of ASTM D1322-19 in the manual apparatus, the operator is to confirm calibration of the apparatus in accordance with ASTM D1322-19 Section 10.1.3 or calibrate, if needed, in accordance with ASTM D1322-19 Section 10.1.1 prior to first use of the day. Recalibrate when there has been a change in the apparatus or operator, or when a change of more than 0.7 kPa occurs in the barometric pressure reading. Calibrate the apparatus by testing two of the reference fuel blends specified in ASTM D1322-19 Section 7.4, using the procedure specified in ASTM D1322-19 Section 11 and, if possible, bracketing the smoke point of the sample. If this is not possible, use the two test blends having their smoke points nearest to the smoke point of the sample. Determine the correction factor, f (sometimes referred to as the lamp factor), for the apparatus from the following Equation (1):

$$f = [(As/Ad) + (Bs/Bd)]/2 \quad (1)$$

where:
As=the standard smoke point of the first reference fuel blend,
Ad=the smoke point determined for the first reference fuel blend,
Bs=the standard smoke point of the second reference fuel blend, and
Bd=the smoke point determined for the second reference fuel blend.

According to Section 10 of ASTM D1322-19 in the method employing the automated apparatus, the automated apparatus may automatically calculate the correction factor f according to Equation (1) using stored reference data. The apparatus shall have a calibration database for the storage of the reference fuel blends values specified in TABLE 1 from ASTM D1322-19.

TABLE 1

Reference fuel blends

| Standard Smoke Point at 101.3 kPa mm | Toluene % (V/V) | 2,2,4-trimethylpentane % (V/V) |
| --- | --- | --- |
| 14.7 | 40 | 60 |
| 20.2 | 25 | 75 |
| 22.7 | 20 | 80 |
| 25.8 | 15 | 85 |
| 30.2 | 10 | 90 |
| 35.4 | 5 | 95 |
| 42.8 | 0 | 100 |

Each calibration test performed with the reference fuel blends shall be stored in this database in addition with the barometric pressure observed at the moment the calibration was performed. ASTM D1322-19 Section 10.2.1 discloses the automated apparatus shall have the capability to automatically calculate the correction factor f according to Equation (1) by automatically selecting in its calibration database the reference fuel blends values specified in TABLE 1, using the procedure specified in Section 11 and the calculation specified in Section 12 and, if possible, bracketing the smoke point of the sample. If this is not possible, it shall use the two test blend results having their smoke points nearest to the smoke point of the sample. The digital camera and the associated software replace the operator's eyes for the observation of the flame. Consequently, it is not necessary to recalibrate the automated apparatus when there has been a change in the operator.

ASTM D1322-19 Section 12 discloses to calculate the smoke point (to the nearest 0.1 mm) via the following Equation (2):

$$\text{Smoke point} = L \times f \quad (2)$$

where:
L=the average of three individual flame height readings, and f=the correction factor of ASTM D1322-19 Section 10.1.2.

With the manual apparatus, the operator does this calculation. The automated apparatus, however, automatically calculates the smoke point.

However, with respect to the automated apparatus, ASTM D1322-19 Section 10.2.2 discloses to record the barometric pressure and check in the calibration database that the instrument has been calibrated at that recorded pressure +/−0.7 kPa. If no calibration values exist for the seven blends specified in Table 1 at the pressure observed +/−0.7 kPa, ASTM D1322-19 Section 10.2.2 discloses to calibrate the apparatus in accordance with Section 10.2.3. If calibration values exist for the seven blends specified in Table 1, in other words, if the instrument has been already calibrated at the pressure observed, ASTM D1322-19 discloses to check the apparatus in accordance with Section 10.2.4. The automated apparatus stores the smoke points obtained with the reference fuels at different barometric pressures. Thus, if the instrument has been already calibrated at the pressure observed it is not necessary to recalibrate the apparatus when a change of more than 0.7 kPa occurs in the barometric pressure reading. Depending on the barometric pressure entered at the test initiation, the apparatus will automatically use the correct stored values obtained with the fuel blends. If the correct values are not yet stored, the apparatus will prompt the operator in order to perform the calibration at the pressure observed again according to ASTM D1322-19 Section 10.2.3 which discloses to calibrate the apparatus by testing the seven reference fuel blends specified in Section 7.4, using the procedure specified in Section 11.

Thus, the conventional method requires a new calibration of the device if the pressure has varied by more than 0.7 kPa (manual method ASTM D1322-19 Section 10.1) or if the calibration database of the automated apparatus has no saved calibration values within 0.7 kPa of atmospheric pressure at the time of the test (ASTM D1322-19 Section 10.2.2).

Even if the (automated) testing apparatus records the calibration values at different atmospheric pressures, it remains a constraint to have to calibrate with the seven different reference fuel blends, before performing the smoke point measurement on the particular fuel sample to be tested, when there is no saved (stored) calibration values carried out at a pressure close to the current pressure.

For example, as the smoke point value of the fuel sample to be tested is not known in advance, this requires (in theory) to have all values (i.e., called calibration values) of the seven different reference fuel blends at atmospheric pressure equivalent to that at which the testing procedure measurement is to be performed. This is tedious because it is difficult to have all the calibration values with steps of 0.7 kPa and, therefore, frequently requires calibrations at the right pressure before conducting the test method. For this reason, many test operators simplify the calibration process (i.e., "cheat") by entering a pressure value having existing calibrations values.

It would be desirable to provide a device and method for improved automatic correcting of the smoke point measurement.

SUMMARY

ASTM D1322-19 does not describe any correction as a function of humidity or temperature. ASTM D1322-19 says the automated device shall have a calibration database for the storage of reference fuel blends values specified in its Table 1 to correct for air pressure at the time of measurement. The ASTM D1322-19 calibration process is mainly made to compensate for variations in atmospheric pressure.

This also includes a correction of intrinsic parameters to each device but that does not vary over long periods. With a manual apparatus or current automated apparatus, the operator measures current air pressure with a separate barometer and manually inputs the measured value into the apparatus. The ASTM D1322-19 measurement correction is based on a comparison with the deviation measured on its reference products (Reference fuel blends, mix 1 to mix 7) under the same conditions as the test to be performed. The correction is accurate if the test is carried out under the same conditions. However, in reality this is typically not the case because the calibrations are stored and thus based on tests that were performed days, months or even years prior to the current test and only atmospheric pressure is recorded at the time of the calibration test, but not other variables that may impact results, for example humidity, temperature or other parameters.

Calibrations are used to compensate for measurement biases by comparing them with reference pressure values of 101.3 kPa. However, a source of bias that may affect the final results in measurement of the smoke point is caused by the humidity of the atmosphere at which the calibration is performed. Conventional devices and methods do not measure and record humidity conditions so they do not reduce or eliminate bias or error caused by humidity. Thus, even when it is known that a particular test is being carried out on a kerosene at the same pressure as during or contemporaneous with the calibration, humidity conditions may be different (since humidity is not measured and recorded). This will generate smoke point measurement errors, and alter the repeatability of the tests.

Air humidity and ambient temperature may significantly impact (influence) the results when measuring smoke point pursuant to the test method. For example, it is difficult to conduct the test method with known testing apparatuses in geographies having high humidity (e.g., Southeast Asia during monsoon season) because the measurements during the calibration are outside the authorized limits of the ASTM D1322-19 standard.

The invention automatically corrects for the effects of atmospheric conditions on the measurement of the smoke point by the ASTM D1322-19 standard or its equivalents, such as ISO 3014, IP 57, NF M 07-028, etc. There is no (or very little) difference between the ASTM D1322-19 standard and the ISO, IP, NF, GOST, JIS, etc. equivalent standards. The present device and method comply with these equivalent standards. Thus, an apparatus for determining the smoke point conforming to the specifications of an ASTM D1322-19 standard is also an apparatus for determining the smoke point conforming to the specifications of the equivalent standards. Thus, a method for determining the smoke point conforming to the specifications of an ASTM D1322-19 standard is also a method for determining the smoke point conforming to the specifications of the equivalent standards.

The invention automatically corrects for the effects of humidity on the measurement of the smoke point. Preferably the invention automatically corrects for the effects of humidity and pressure on the measurement of the smoke point.

The present invention provides a device and method for automatically correcting the smoke point measurement (flame height typically in millimeters) according to atmospheric conditions, for example the device and method automatically corrects for ambient (atmospheric) air temperature and humidity. In particular, the present invention takes the humidity factor into account to eliminate the induced error due to variations in humidity. The amount of water molecule in the air, disrupts the combustion of kerosene and therefore the value of the smoke point. The density of water vapor in the air is called absolute humidity and is expressed in Kg/m3. The humidity sensors deliver the relative humidity (RH) expressed in % RH. To calculate the absolute humidity from the relative humidity is well documented in the art. To calculate the absolute humidity from the relative humidity involves the air temperature and atmospheric pressure measured at the same time as the relative humidity. Thus, the inventive device has sensors to measure relative humidity, the air temperature and typically atmospheric pressure. However, it should be noted that atmospheric pressure has very little influence on this calculation of absolute humidity (less than 0.1% for a variation of 250 hPa).

The invention corrects for variations of atmospheric conditions and other factors to allow correcting for all influencing factors. The present invention automatically corrects the measured smoke point values for humidity and temperature. The invention corrects the measured smoke point values (flame height in mm) as a function of a difference between the calculated absolute humidity and a normalized absolute humidity. The invention preferably choses to normalize the smoke point measurements at 7 gr/m$^3$ absolute humidity because it is the typical value for the reference mixtures. But this can be another value, typically a normalization value of absolute humidity of 0 to 40 gr/m$^3$. The invention corrects the measured smoke point values (flame height in mm) in existing calibrations as a function of the difference between current atmospheric pressure measured by an external barometer or an integrated sensor, and the pressure recorded during calibration. The pressure measurement is also used for a real-time correction of the flame height measurement and to normalize the smoke point measurements at 101.3 kPa (also known as 1013 hPa (hectopascals) or 1 atm). The invention preferably choses to normalize the smoke point measurements at 1013 hPa because it is the typical value for the reference mixtures. But this can be another value, typically a normalization value of atmospheric pressure on the planet Earth between 800 and 1100 hPa.

The invention also integrates an air humidity sensor and an ambient temperature sensor in the inventive device, and uses the measured values to correct the flame height measurement. The correction can be applied in real time during the flame height measurement or on the smoke point result. Also, an atmospheric pressure sensor may be integrated in the device of the present invention. However, atmospheric pressure may also be read on an external barometer and its value entered into the device. The integration of the pressure sensor mainly avoids operator errors in reading the barometer or operator typing errors when entering. The integration of the pressure sensor also ensures better traceability of the test.

Preferably the present invention not only corrects the measured smoke point values for humidity and temperature but also corrects for atmospheric pressure to avoid having to do (or to have done previously and stored) calibrations for every time the pressure varied more than ±0.7 kPa from the pressure during calibration.

There are differences between the inventive pressure correction and the correction currently applied by the ASTM D1322-19 standard. The ASTM D1322-19 standard, by indicating that the calibrations must be redone when the pressure changes by more than 0.7 kPa, has implicitly created a link between the calibration process with the reference mixtures and the atmospheric pressure.

However, as indicated above the smoke point result is influenced by various factors. There are atmospheric pressure, humidity and errors related to the camera itself used for measuring smoke point such as camera or lens faults or adjustment tolerances.

The ASTM D1322-19 standard employs a lamp factor "f" to account for errors related to the camera itself used for measuring smoke point such as camera or lens faults or adjustment tolerances and it purports to account for changes in pressure by requiring that the calibrations be redone when the pressure changes by more than 0.7 kPa. However, there is a need to improve this to account for other atmospheric factors. There is also a need for a better way to accommodate pressure variations to avoid the need to redo the calibrations when the pressure changes by more than 0.7 kPa from the time of the original calibration to the time of the test sample measurement.

The ASTM D1322-19 standard corrects the measurement result of the smoke point by comparing it to the results obtained with two reference mixes (bracketing the result), and applying for correction, the average of the measurement deviations obtained on the mixtures with respect to values of reference of these mixtures.

This would be accurate if the measurements on the mixtures (called calibrations) and the measurement on the kerosene to be tested are carried out under the same conditions, i.e., the same pressure and same humidity. However, the ASTM D1322-19 standard does not take humidity into account, and requires that the calibrations be repeated only to keep a near atmospheric pressure between the test and the calibrations. This potentially generates errors in the measurement of the smoke point of a kerosene.

For example, if the calibrations are carried out at a pressure 980 hPa and a humidity of 9 gr/m$^3$, and the smoke point test is carried out at a pressure also of 980 hPa but a humidity of 21 gr/m$^3$, applying the system of the standard, the result will be corrected by a value X which corresponds to the condition 980 hPa and 9 gr/m$^3$. This will not be correct because this value X does not take into account the difference of 12 gr/m$^3$ of humidity between the calibrations and the measurement of the smoke point.

The inventor discovered that humidity has a very strong influence on the result and poses significant problems of reproducibility of the tests. To correct this problem, the invention takes humidity into account by measuring humidity during or contemporaneous with calibration and tests and applying a humidity correction factor $f_h$. Thus, the inventor studied the influence, on the smoke point result, of humidity (and only humidity, while maintaining the variables due to other possible influences constant). From this study the inventor deduced an absolute humidity correction formula employing the correction factor $f_h$ to correct the result of the measurements as a function of absolute humidity. The humidity correction formula employing absolute humidity correction factor $f_h$ can be empirically determined from data. Potentially the humidity correction formula employing humidity correction factor $f_h$ can be theoretically determined. This humidity correction formula is not taught or suggested by the conventional ASTM D1322-19 standard process.

Thus, a first aspect of the invention is to determine absolute humidity, using the measurement of relative humidity, ambient temperature and ambient atmospheric pressure to calculate absolute humidity. Calculation of absolute humidity is well known in the art. However, the inventor notes that atmospheric pressure has a negligible impact in this measurement of absolute humidity. Although not preferred, some methods simplify calculating absolute humidity by assuming a standard pressure such as 1013 hPa (1 atm) rather than employing the measured atmospheric pressure.

Then the invention applies a humidity correction, as a function of a difference between this absolute humidity and a normalized absolute humidity value, to the smoke point (flame height) measurements carried out to obtain comparable measurements in which the influence of absolute humidity has been eliminated.

Thus, the invention adapts the standard process for the ASTM D1322-19 standard to work even if the calibrations and tests are carried out under different humidity conditions.

However, there is still the problem generated by the need to have the calibrations carried out at pressures close to the test pressure and therefore to often have to make calibrations before a test.

A preferred second aspect of the invention is employed to solve this problem. The purpose of this is to eliminate the need to re-calibrate each time the pressure varies by more than 0.7 kPa.

The second aspect of the invention is to make only one calibration set for the 7 reference mixes and to be able to use them whatever the atmospheric pressure during the measurement by recalculating the calibration values as a function of the pressure by applying a pressure correction factor $f_p$. This is only possible if the first aspect of the invention in which the influence of humidity is removed is also employed. In the context of the present specification the term "during the test" encompasses simultaneous or contemporaneous with the test. Contemporaneous including the same day or within +/−1 hour of the test.

However, even if the first aspect of the invention to correct for humidity is applied, the influence of pressure on the result was unknown and how to correct the influence of pressure on the result was unknown. The ASTM D1322-19 standard does not teach a formula to apply a correction according to the pressure variation.

Thus, the inventor studied the influence, on the smoke point result, of pressure (and only pressure, while maintaining the variables due to other possible influences constant). From this study the inventor deduced a pressure correction formula employing a pressure correction factor $f_p$ to correct the result of the measurements as a function of pressure. The pressure correction formula employing pressure correction factor $f_p$ can be empirically determined from data. Potentially the pressure correction formula employing pressure correction factor $f^p$ can be theoretically determined. This pressure correction formula is not taught or suggested by the conventional ASTM D1322-19 standard process. It is different from the implicit pressure correction of the conventional ASTM D1322-19 standard. The conventional ASTM D1322-19 standard may incorrectly account for pressure because it does not account for humidity variations. The conventional ASTM D1322-19 standard has the need to re-calibrate each time the pressure varies by more than 0.7 kPa and even if there is a recalibration it does not account for humidity variations.

The invention may apply its pressure correction in different ways, described in the present specification. The smoke point measurements may be normalized to 1013 hPa (1 atm) or another suitable pressure for normalization. This normalization at 1013 hPa is not essential but facilitates the comparison of the results. Therefore, preferably the invention applies its pressure correction and records normalized calibrations at 1013 hPa, by either (method 1, described in more detail elsewhere in this specification) having the 3 measurements corrected and averaged thereafter, or (method 2, described in more detail elsewhere in this specification) making the 3 measurements without correction as a function of the pressure and by correcting the average. The invention can then correct the result of a test as a function of the pressure by correcting the measurement (for 1013 hPa) and applying the calibration already stored at 1013 hPa which corresponds to method 1, or by not correcting the measurement as a function of the pressure and recalculating the calibration values from 1013 hPa to the pressure during the test which corresponds to method 2.

As a result the present invention does an initial calibration of the apparatus to calculate a correction factor f (also known as lamp factor) according to paragraph 10 of ASTM D1322-19 standard. This correction factor f only corrects for the intrinsic errors of the camera such as faults in the camera, the lens or the settings specific to each apparatus. An operator of the inventive device or method would keep these calibrations for this reason, and also to remain compliant with the standard. The calibration and lamp factor system described in the standard is not a correction depending on the pressure, but the application to the smoke point measurement result, of the specific to each apparatus deviations noted (whatever the cause) during the measurement at pressure close to that on the reference mixtures. In doing this initial calibration the operator should note the ambient humidity, temperature, and pressure.

Thus, the invention provides a testing device and method for determining smoke point of a hydrocarbon. The device including: an apparatus for determining the smoke point conforming to specifications of an ASTM D1322-19 standard, imaging device for taking a series of digital images of a flame;

ambient relative humidity sensor for measuring relative humidity;

ambient temperature sensor for measuring temperature;

computer system linked to the imaging device, humidity sensor, and temperature sensor programmed to analyze digital images from the imaging device to measure flame height flame, and use temperature with relative humidity measured by the temperature and humidity sensors to calculate absolute humidity and correct measured flame height as a function of difference between the calculated absolute humidity and normalized absolute humidity, and preferably to correct measured flame height as a function of difference between pressure during flame height measuring and normalized pressure. Typically the normalized absolute humidity value is a value in a range of 0 gr/m$^3$ to 40 gr/m$^3$, preferably 7 gr/m$^3$. Typically the normalized pressure value is a value between 800 and 1100 hPa, preferably 1013 hPa.

The invention also provides a testing device for determining smoke point of a hydrocarbon corrected for pressure, comprising:

an apparatus for determining the smoke point conforming to the specifications of an ASTM D1322-19 standard, means for taking a series of digital images of a flame;

an ambient pressure sensor for measuring ambient pressure;

a computer system linked to the means for taking the series of digital images of a flame, linked to the ambient pressure sensor, the computer system programmed to enable digital images taken by the means for taking a series of digital images to be analyzed to measure flame height, and for using pressure measured by the pressure sensor to correct measured flame point values of the hydrocarbon based on ambient pressure measured by the ambient pressure sensor as a function of a difference between a current ambient pressure measured by the pressure sensor during testing and a normalized pressure ambient pressure. The invention also provides a method for using the testing device for determining smoke point of a hydrocarbon corrected for pressure.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
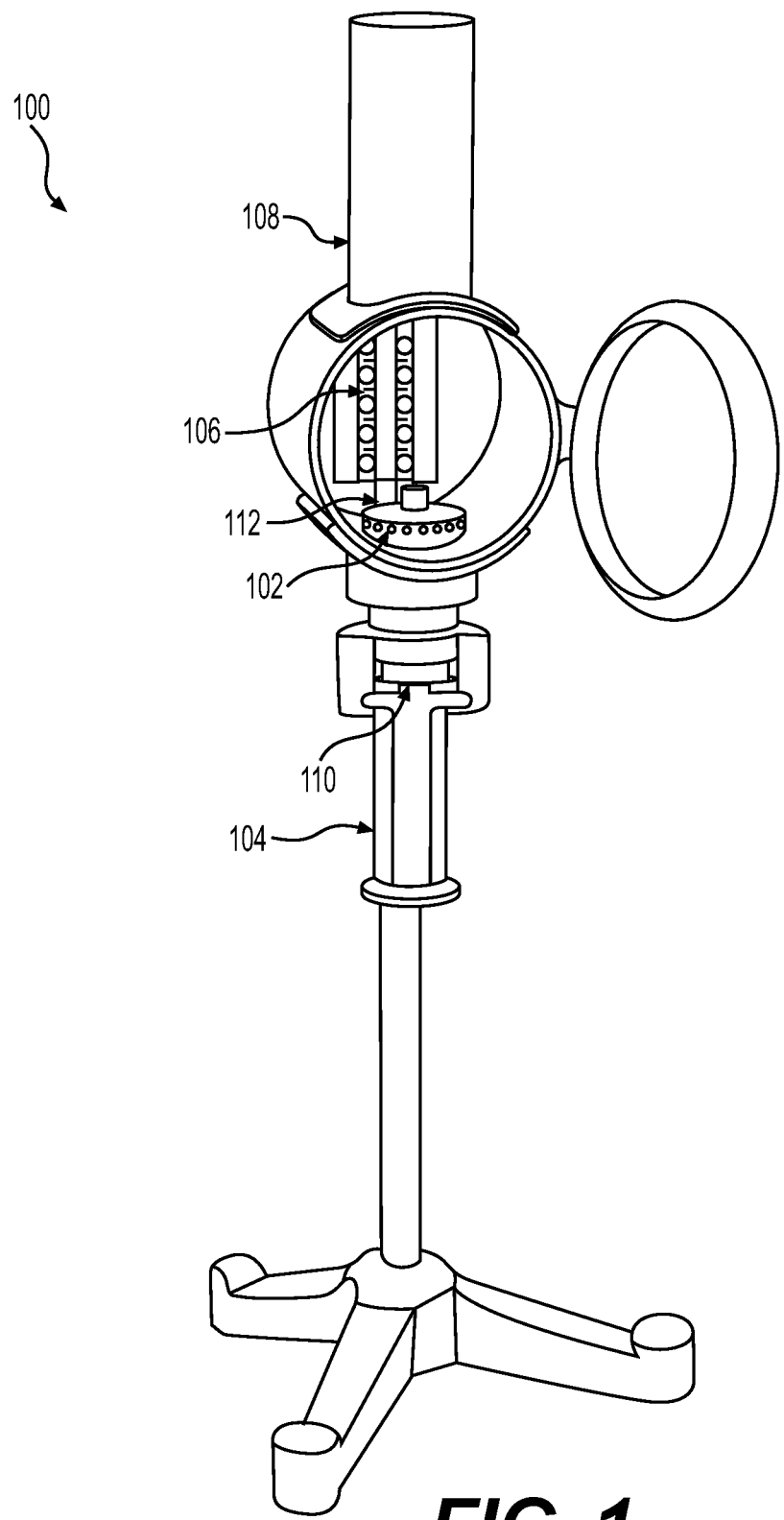
FIG. 1 is an isometric view of an example of a prior art manual smoke point testing apparatus.

The present disclosure is related to hydrocarbon smoke point measurement devices and, more particularly, to devices and methods for automatically correcting the smoke point measurement according to atmospheric conditions.

The invention herein described is directed to devices and methods for automatically correcting the smoke point measurement according to atmospheric conditions or parameters, such as, atmospheric pressure, ambient temperature, and/or air humidity. The testing apparatus includes a humidity sensor and an ambient temperature sensor that measure atmospheric conditions (i.e., humidity and temperature) and such measured values (data) may be utilized to correct the flame height measurement. Thus, the invention typically corrects measured smoke point values (flame height in mm) in existing calibrations as a function of the difference between current atmospheric humidity measured by an integrated humidity sensor of the testing apparatus (converted to absolute humidity) and a normalized absolute humidity standard value. The invention preferably also corrects measured smoke point values (flame height in mm) in existing calibrations as a function of the difference between current atmospheric pressure measured by a pressure sensor, preferably an integrated pressure sensor of the testing apparatus, and the pressure recorded during calibration. The pressure measurement may also be used for a real-time correction of the flame height measurement and to normalize the smoke point measurements at typically 101.3 kPa (1 atm, 1013 hPa). Preferably the selected normalized pressure value is 1013 hPa, but it can be selected as any value between 800 and 1100 hPa.

The standard test method for smoke point of kerosene and aviation turbine fuel is set forth in ASTM D1322-19, Standard Test Method for Smoke Point of Kerosene and Aviation Turbine Fuel, ASTM International (April 2018), or its equivalent(s) (collectively, the "test method"). The test method generally comprises burning a fuel sample in a testing apparatus and then measuring the maximum height of the resulting flame that can be achieved with the fuel sample without smoking. The testing apparatus generally comprises an enclosed wick-fed lamp that is calibrated against pure hydrocarbon blends of known smoke point. The testing apparatus may be a manual test apparatus or an automated testing apparatus, and the test method prescribes procedures for utilization of either such testing apparatus.

More specifically, the test method comprises the following steps: (i) preparing the testing apparatus as described in Section 9 of the ASTM D1322-19 test method; (ii) calibrating the testing apparatus as described in Section 10 of the ASTM D1322-19 test method; (iii) testing the fuel sample via the procedures set forth in Section 11 of the ASTM D1322-19 test method; and (iv) calculating the smoke point as described in Section 12 of the ASTM D1322-19 test method; and (v) reporting the results as described in Section 13 of the ASTM D1322-19 test method. As mentioned above, the particular procedures of the foregoing steps may depend on whether the testing apparatus is a manual test apparatus or an automated testing apparatus.

FIG. 1 illustrates an exemplary conventional manual smoke point testing apparatus 100 for testing the fuel sample in accordance with Section 11 of the ASTM D1322-19 test method.

Referring to FIG. 1, the conventional (manual smoke point) testing apparatus 100 includes a gallery 102 and a candle 104 that is movable into the gallery 102. The candle 104 comprises a tank filled with the fuel sample (i.e., test sample) and supports a wick W (see FIG. 2) that is soaked with the test sample when dipped in the tank of the candle 104. The candle 104 may move then position the fuel soaked wick into the gallery 102 where it will be lit for smoke point testing. Accordingly, a flame is produced within the gallery 102 and, as shown, a graduated scale 106 is provided within the gallery 102 for measuring the height of the flame. Also, a chimney 108 may be provided on the gallery 102 to vent resulting combustion gases and fumes. The candle 104 is introduced into the gallery 102 before being lit. A candle socket 110 is provided on the gallery 102 for receiving and supporting the candle 104. A wick guide 112 in fluid communication with the candle socket 110 is provided within the gallery 102 for directing and introducing the wick W into the gallery 102. The position of the candle 104 is vertically positionable within the candle socket 110 to thereby control or vary the amount of wick W extending from the wick guide 112 and, thereby, the amount of wick W exposed within the gallery 102 to be lit on fire during the test method. By adjusting the length of the wick W extending out of the wick guide 112, the size of the flame may be controlled as may be needed when conducting the test method.

When using the (manual smoke point) testing apparatus 100, the flame height $L''$ of the test sample at smoke point is visually read (measured) via the graduated scale 106, and three such observations of the flame height $L''$ (i.e., $L^1$, $L^2$, $L^3$) are made per Section 11.5 of the ASTM D1322-19 test method and then averaged together to calculate the average reading "L". Then, corrected smoke point is calculable by multiplying the average smoke point reading by the correction factor "f" (sometimes referred to as the lamp factor).

Figure 2:
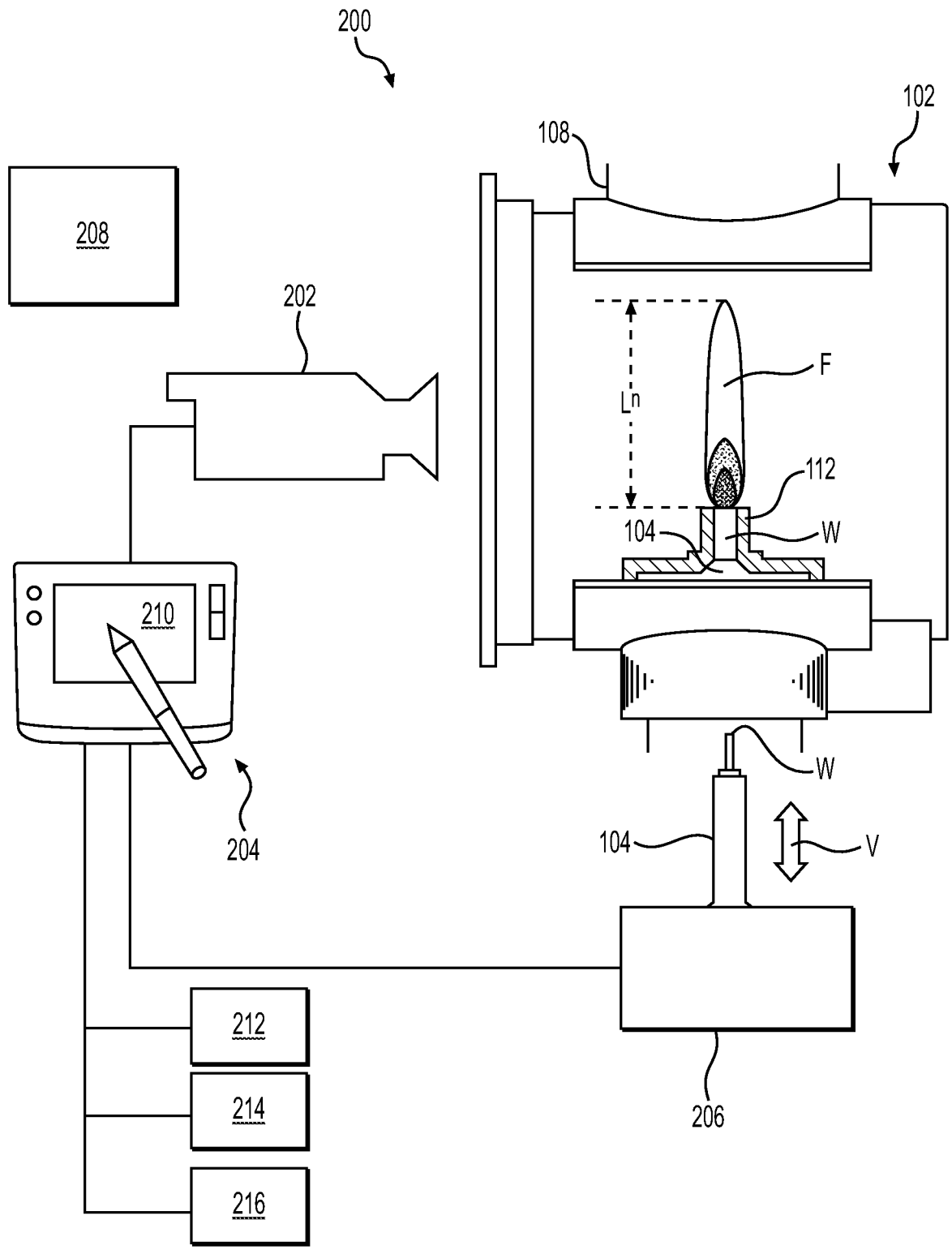
FIG. 2 is schematic of an example of an automated smoke point testing apparatus of the invention for automatically correcting the measured smoke point value as a function of atmospheric conditions, according to the present invention.

FIG. 2 is a schematic of an automated smoke point testing apparatus 200 (hereinafter, the testing apparatus 200) configured to automatically correct the measured smoke point values as a function of atmospheric conditions, according to the invention. The testing apparatus 200 may be utilized for testing the fuel sample in accordance with procedure of Section 11 of the ASTM D1322-19 test method (i.e., for carrying out step iii).

Figure 2A:
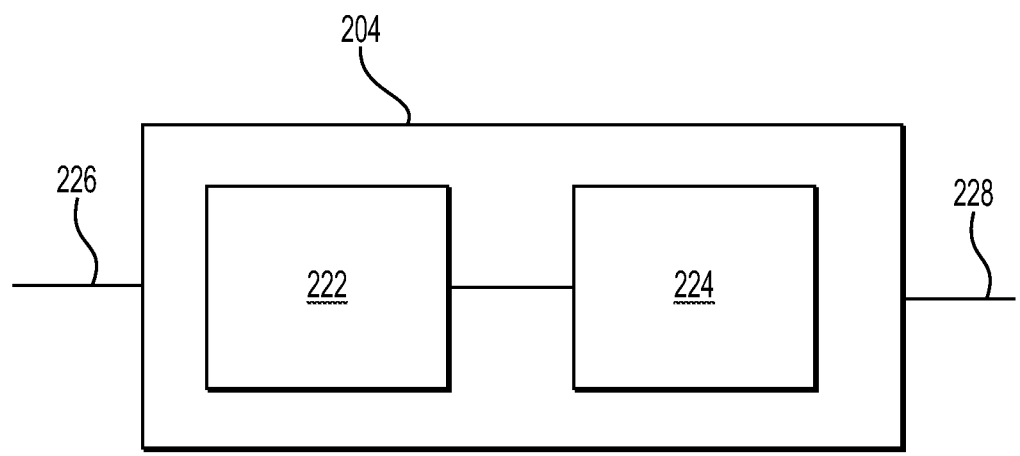
FIG. 2A is schematic of a computer.

The testing apparatus 200 includes a digital camera 202 and a computer 204. As seen in FIG. 2A, the computer 204 comprising a microprocessor 222, memory storage 224, one or more data/signal inputs 226 for example, for receiving signals from the sensors 212, 214, 216 and the digital camera 202, and one or more data/signal outputs 228 for example, for reporting corrected smoke point of a hydrocarbon or for controlling the candle displacement system 206. The digital camera 202 may comprise a photo detecting charge-coupled device (CCD), complementary metal-oxide-semiconductor (CMOS) image sensor or other imaging sensor, which preferably covers wavelengths in a range from the ultraviolet to the infrared. Optionally the digital camera 202 has a zoom. However, the digital camera 202 may be differently configured. During the test method, the wick W of the candle 104 is soaked with the fuel sample and then lit on fire to produce a flame F. The digital camera 202 is positioned relative to the gallery 102 and appropriately aimed such that it may capture (record) an image (or video) of the flame F flaring from the wick W that extends upward from the wick guide 112. The digital camera 202 is connected to the computer 204, which has software for analyzing imagery received from the digital camera 202 to determine (measure) and record a height of the flame F. In addition, the testing apparatus 200 includes a candle displacement system 206 for adjusting the height ("$L'''$") of the flame F. The candle displacement system 206 may be a motorized conveyer system for raising the candle 104 higher within the gallery 102, to thereby increase (or decrease) the amount of the wick W protruding from the wick guide 112, which has the effect of increasing (or decreasing) the size (height) of the flame F. The displacement system 206 may vertically translate the candle 104 as shown by directional arrow V, to control the amount of wick W exposed within the gallery 102 for combustion. In the illustrated example, the candle 104 has been illustrated both when positioned below (outside) the wick guide 112 with no flame F on the wick W, and when positioned inside the wick guide 112 where the flame F with the height $L''$ having been generated on the wick W within the gallery 102

The testing apparatus 200 may further comprise an anti-infrared filter (not shown) placed between the flame F and the digital camera 202 for taking the series of digital images.

The testing apparatus 200 is configured to automatically correct the measured smoke point values as a function of the atmospheric conditions of humidity and temperature and typically also pressure. Referring again to FIG. 2, the testing apparatus 200 is shown having a relative humidity sensor 212 for measuring relative atmospheric humidity, a temperature sensor 214 for measuring ambient temperature, and a pressure sensor 216 that measures ambient atmospheric pressure during flame height measurement, or contemporaneous (currently) with the flame height measurement such as the day of taking the digital images or within an hour before or after taking the digital images. Also, the relative humidity sensor 212, the temperature sensor 214, and the pressure sensor 216 are in communication (e.g., connected with wires or via one or more various wireless communication protocols) to the computer 204. Thus, the computer 204 may receive data indicative of the current relative atmospheric humidity (via the humidity sensor 212), the current ambient temperature (via the temperature sensor 214), and the current atmospheric pressure (via the pressure sensor 216). FIG. 2 shows the humidity sensor 212, the temperature sensor 214, and the pressure sensor 216 integrated within the testing apparatus 200 and connected to the computer 204. However, any one or more of the relative humidity sensor 212, the temperature sensor 214, and the pressure sensor 216 need not be integrated within the testing apparatus 200. However, utilization of an integrated pressure sensor would inhibit the test operator from entering incorrect (albeit convenient) pressure data. Where the automatic pressure correction of the present invention is not employed, utilization of an integrated pressure sensor would also ensure that the test operator performs a new calibration at pressure if no corresponding calibrations values exist. The humidity sensor 212 and the temperature sensor 214 are utilizable to compensate for the influence of humidity on the resulting measurement of smoke point.

The humidity sensor 212, the temperature sensor 214, and the pressure sensor 216 may each be provided as a separate component. However, one or more of the humidity sensor 212, the temperature sensor 214, and/or the pressure sensor 216 may be integrated and combined together as an individual component. For example, the humidity sensor 212 and the temperature sensor 214 may be integrated together and provided as an individual component. In other examples, the temperature sensor 214 and the pressure sensor 216 may be integrated together and provided as an individual component. Integrating the temperature sensor 214 with either the humidity sensor 212 and/or the pressure sensor 216 allows for compensation of internal thermal drifts.

The pressure sensor 216 need not be integrated within the test apparatus 400 and connected to the computer 204. Rather, the test operator may utilize other means of measuring atmospheric pressure, such as the optional barometric pressure acquisition system 208, and then manually enter atmospheric pressure to the computer 204, for example, via the data input 210

The computer 204 includes software for automatically correcting drifts in the smoke point measurement result that may be caused by temperature, humidity, and optionally other atmospheric parameters such as pressure. The computer 204 automatically corrects the measured smoke point result as a function of either or both of the following: (a) the difference between absolute humidity, calculated from the relative humidity measured by the humidity sensor 212, and the ambient temperature measured by the temperature sensor 214, and/or (b) a difference between a current atmospheric pressure measured by the pressure sensor 216 during or contemporaneous with testing and a normalized pressure value.

Figure 4A:
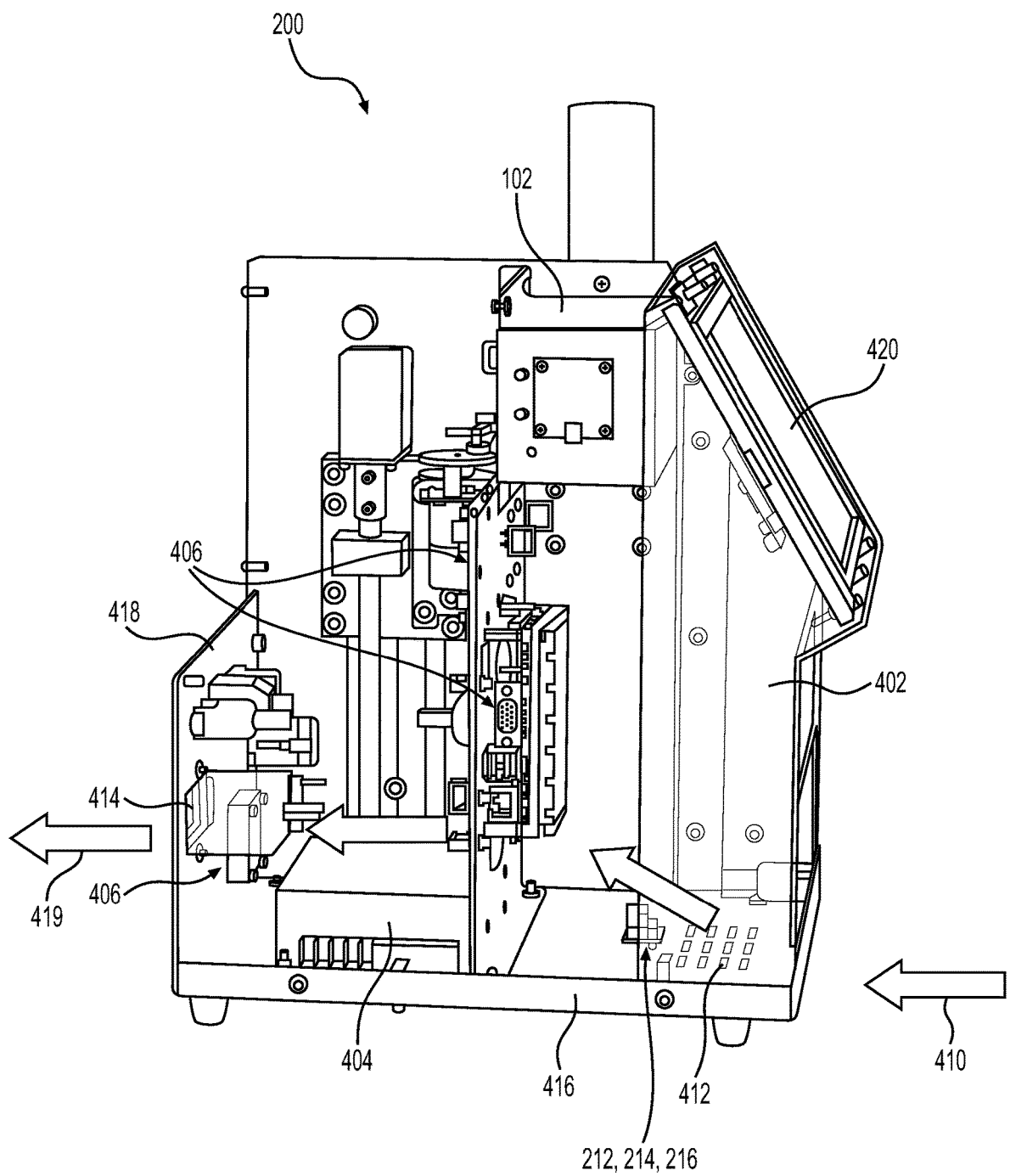
FIGS. 4A-C show an exemplary configuration of the automated smoke point testing apparatus of FIG. 2.
Figure 4B:
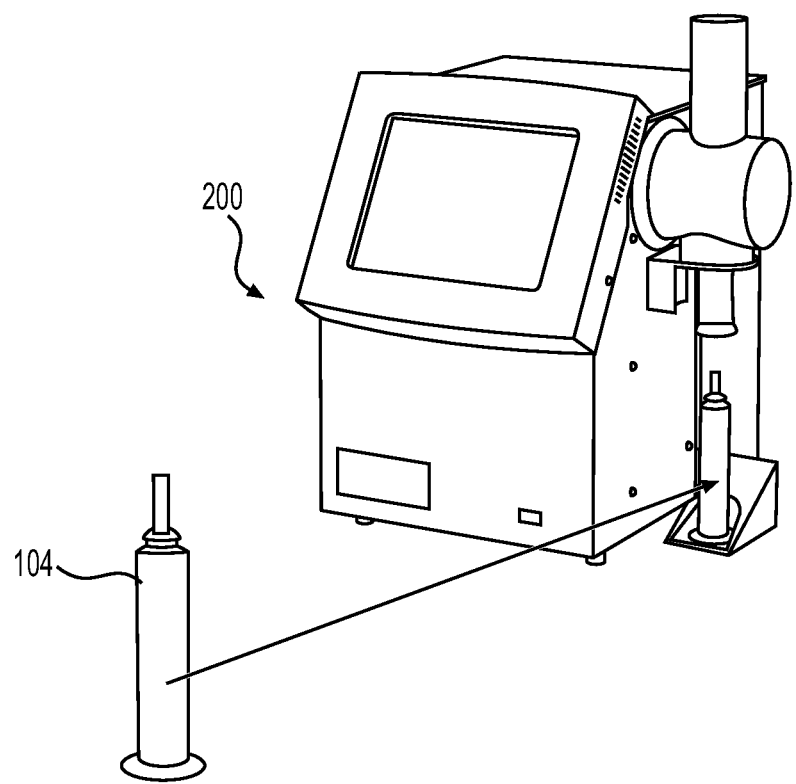
Figure 4C:
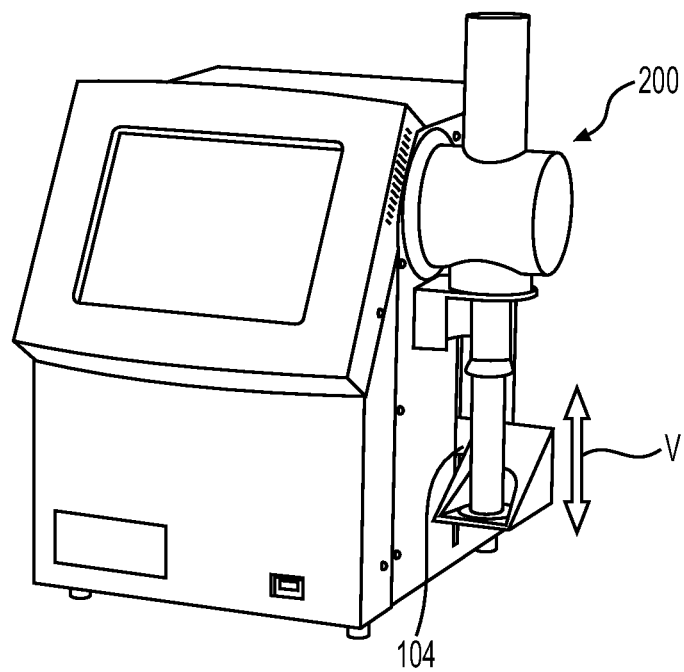

FIGS. 4A-4C also illustrate an exemplary configuration of the testing apparatus 200, according to one or more embodiments of the present disclosure. In the illustrated embodiment, the testing apparatus 200 includes a housing 402, a power supply 404, and electronics 406 including the computer 204 (FIG. 2) having a microprocessor 222 for performing calculations based on measurements from sensors 212, 214, 216 of the apparatus 200 as well as memory 224 (FIG. 2A). Because the power supply 404 and/or the electronics 406 may generate heat within the housing 402, the testing apparatus 200 may be provided with ventilation means. For example, the testing apparatus 200 may include a fan 408 arranged to create an air flow 410 through the housing 402, from an air intake vent (or inlet) 412, where the air flow 410 is at ambient temperature and enters the housing 402, to an exhaust vent (or outlet) 414, where the air flow 410 that has been heated within the test apparatus 200 is discharged as heated air flow 419 out of the housing 402. Here, the intake vent 412 is positioned on a chassis 416 at a lower side of the housing 402, and the fan is positioned at a rear wall 418 of the housing 402 to pull the air flow 410 into the housing 402 via the intake vent 410, through the housing to the exhaust vent 414 where it is discharged. The testing apparatus 200 also has a display screen 420, such as a touch screen for entering or receiving information or commands or displaying information such as test results or other parameters.

One or more of the humidity sensor 212, the temperature sensor 214, and/or the pressure sensor 216 may be positioned proximate to the intake vent 412. In the illustrated embodiment, all of the sensors 212, 214, 216 are positioned inside the housing 402 at a position on the chassis 416 proximate to the air intake vent 412. In this manner, the air flow 410 entering the housing 402 and interacting with the sensors 212, 214, 216 is "new" air representative of the actual air temperature outside of the housing 402. Thus, the sensors (i.e., the temperature sensor 214) may analyze such "new" air that is at a temperature indicative of actual ambient air temperature, before such "new" air is subsequently routed through the housing 402 to cool the various internal componentry of the testing apparatus 200, such as the power source 404 and/or the electronics 406 which may heat the "new" air above the actual ambient air temperature. In addition, placing the intake vent(s) 410 in a position where they may capture air from under the test apparatus 200, for example, on the chassis 416 as illustrated, makes it possible to measure air temperature that is most representative of the actual ambient air temperature of air that is ultimately combusted within the lamp during the test method.

Figure 3:
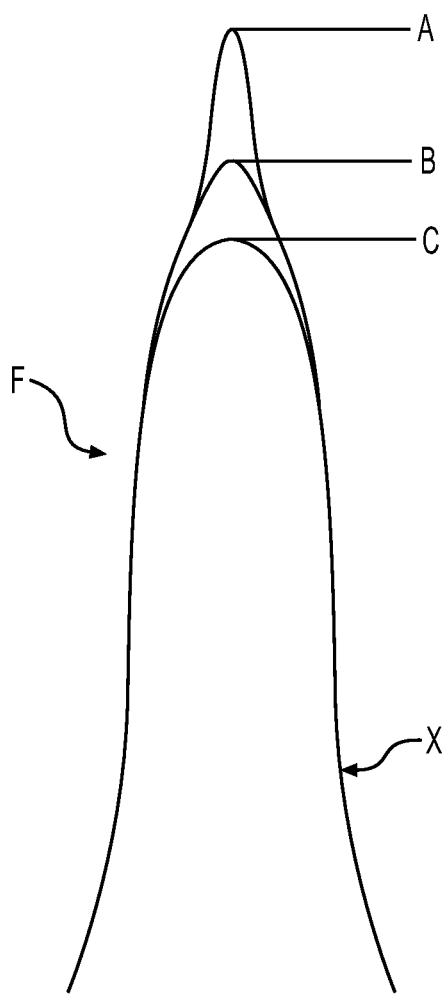
FIG. 3 shows examples of typical flame appearances.

FIG. 4B shows the testing apparatus 200 provided with the elements of FIGS. 2 and 4A when the candle 104 is a first position. FIG. 4C shows the testing apparatus 200 provided with the elements of FIGS. 2 and 4A when the candle 104 is a second position inserted into the testing apparatus 200. To use the testing apparatus 200, move the candle 104 from a first position away from the testing apparatus 200 shown in FIG. 4B to a second position on a conveyor of the candle displacement system 206 of the testing apparatus 200 as shown on FIG. 4C. Key in all sample details, if needed, and initiate the test which will result in at least some automatic measurement of current atmospheric parameters. For more details, refer to the instruction manual of the apparatus manufacturer. The candle is automatically introduced in the lamp and undergoes the flame appearance sequence specified in ASTM D1322-19 Section 11.5. This includes lighting the candle 104. Then the candle level is automatically adjusted so that the flame is approximately 10 mm high and the lamp burns for 5 minutes. After the 5 min stabilization time, the candle is automatically raised until a smoky tail appears, then it is lowered slowly through the following flame appearance sequence. A long tip; smoke slightly visible; erratic and jumpy flame. FIG. 3 shows a flame "F". In FIG. 3, Flame "A" is Too high, Flame "B" is Correct, Flame "C" is Too Low and "X" is the Base of the flame. An elongated, pointed tip with the sides of the tip appearing concave upward as shown in FIG. 3 (Flame A). The pointed tip just disappears, leaving a very slightly blunted flame as shown in FIG. 3 (Flame B). Jagged, erratic, luminous flames are sometimes observed near the true flame tip; these shall be disregarded. A well rounded tip as shown in FIG. 3 (Flame C). Determine the height of Flame B to the nearest 0.5 mm in the manual method or nearest 0.1 mm in the automatic method. Record the height observed.

The software of apparatus 200 analyses flame images taken by the digital camera. It automatically detects the flame shape corresponding to Flame B according to ASTM D1322-19 Section 11.5.3 also shown in FIG. 3. It determines the height of Flame B to the nearest 0.1 mm. The testing apparatus 400 records the height observed. The candle conveyor lowers the candle 104, the flame is automatically extinguished, and the conveyor comes back to its rest position. Due to the flame height resolution of the digital camera, the flame height is recorded to the nearest 0.1 mm. The apparatus makes three separate observations of the flame height at the smoke point by repeating the flame appearance sequence specified in ASTM D1322-19 Section 11.5. If these values vary over a range greater than 1.0 mm, the testing apparatus 400 shall warn the test operator. The test is repeated with a fresh sample and another wick. Remove the candle 104 from the conveyor, rinse with heptane, and purge with air to make ready for reuse.

The computer 204 automatically corrects the measured smoke point result as a function of absolute humidity using data measured by the humidity sensor 212, together with temperature data (e.g., from the temperature sensor 214) and the pressure sensor 216 or barometric pressure acquisition system 208. Accordingly, aspects of the present disclosure improve repeatability of test method and accuracy of smoke point results by factoring in humidity to the smoke point calculations.

Humidity is the atmospheric condition representative of the amount of water molecule in air. Humidity disrupts the combustion of kerosene and, therefore, humidity adversely affects the value of the smoke point. The density of water vapor in the air is called absolute humidity ("AH") and is expressed in $Kg/m^3$. The amount of water vapor present in air expressed as a percentage of the amount needed for saturation at the same temperature is called relative humidity ("RH") and is expressed as a percentage (% RH). The AH may be calculated based on the RH, the ambient air temperature ("T"), and the atmospheric pressure ("P"). Accordingly, the testing apparatus 200 may include the humidity sensor 212 for measuring RH, the temperature sensor 214 for measuring the ambient air temperature T, and the pressure sensor 216 that measures current atmospheric pressure P, and the computer 204 may then use these measurements to calculate AH (via RH to AH conversion formulae; formulae to convert RH to AH are known). A sample calculation of AH is presented in a below-listed section entitled "SAMPLE CALCULATION—Relative humidity to Absolute humidity conversion formula". Also, the computer 204 may use these measurements to apply a humidity correction factor $f_h$ (i.e., an AH-based correction) when performing the smoke point calculations to correct the measured flame height as a function of a difference between the calculated absolute humidity and a normalized absolute humidity value.

It has been observed that atmospheric pressure may have very little influence on the calculation of AH (less than 0.1% for a variation of 250 hPa).

It has also been observed that ambient air temperature T may have significant influence on the resulting calculation. Accordingly, the temperature sensor 214 may be appropriately positioned relative to the testing apparatus 200 (and its envelope) so that the ambient air temperature T measurement is representative of the actual air temperature of the environment where the test method is being conducted.

The invention permits recalibrating the testing apparatus 200 to what the smoke test measurement would have been at the standard (normalized) humidity, wherein the normalized humidity value is a value in a range of 0 $gr/m^3$ to 40 $gr/m^3$, preferably 7 $gr/m^3$.

In the illustrated example, the testing apparatus 200 may utilize a measure of atmospheric pressure such as the pressure sensor 216 or, instead of the pressure sensor 216, the optional external barometric pressure acquisition system 208. The pressure sensor 216 would communicate the ambient air pressure value to the computer 204 (or other control unit). The external barometric pressure acquisition system 208 would obtain (receive) a value of ambient pressure. Then an operator would manually communicate (input or enter) the ambient air pressure value from the external barometric pressure acquisition system 208 to a data input 210 of the computer 204 (or other control unit). For example, the barometric pressure acquisition system 208 may include an external (or separate) barometer for measuring ambient atmospheric pressure to obtain a measured atmospheric pressure value but does not directly feed this measured air pressure value to the computer 204. The test operator may manually enter this measured air pressure value into the data input 210 integrated with the computer 204 so that the computer 204 may use this measured air pressure value. Thus, the data input 210 may comprise a touchscreen, key pad, a dial, or other means by which the test operator may manually input data for use by the computer 204.

According to a preferred aspect of the present invention the computer 204 automatically does a pressure correction to correct the measured flame height employing a pressure correction factor "$f_p$". This automatic pressure correction avoids the recalibration which the ASTM D1322-19 standard indicates must be done when the pressure changes by more than 0.7 kPa. Thus, this automatic pressure correction facilitates testing method performance by not requiring the test operator to perform new calibrations when calibration values at the current pressure ±0.7 kPa are not available, for example, when they are not saved in the calibration database.

Thus, if the inventive method or apparatus uses pressure correction according to the invention there is no need to select the calibration at the pressure closest to the measurement.

However, the user (operator) can still select the calibration at the pressure closest to the measurement if he or she wishes to make several calibrations for the same reference mixture and select the calibration at the closest pressure. The invention permits recalibrating the testing apparatus 200 to what the smoke test measurement would have been at the standard correct atmospheric pressure, typically 101.3 kPa (1 atmosphere). The computer 204 may utilize information entered via the pressure sensor 216 or the data input 210 for use in automatically calibrating the testing apparatus 200 to what the smoke test measurement would have been at the standard correct atmospheric pressure, typically 101.3 kPa (1 atmosphere). Thus, the computer 204 or the barometric pressure acquisition system 208 may be associated with a calibration database to select the right calibration value when automatically calculating the correction factor (lamp factor "f") described below. The calibration database may be stored in a memory of the computer 204.

The present disclosure may also provide devices and methods in which the computer 204 automatically calculates the calibration data at the current atmospheric pressure measured by the pressure sensor 216 during the test performed using the stored calibrations normalized to 1013 hPa.

Performing the Smoke Point Test and Calculating and Correcting Smoke Point for Atmospheric Conditions As can be seen, smoke point value is the measure of the flame height $L''$ at a fine shape at its end, which is the height limit before smoke is generated by the combustion of the test sample. FIG. 3 shows the flame F having a common flame base "X" and various exemplary flame variations extending from the flame base X. In particular, FIG. 3 shows a flame variation "A" having an elongated pointed tip with sides of the tip appearing slightly concave upward. FIG. 3 also shows flame variations "B" and "C", with flame variation B comprising a slightly blunted flame tip and flame variation C having a well-rounded tip. The flame variation A extending from flame base X is too high, whereas the flame variation C is too low. Thus, the test procedure directs the test operator to determine when the flame F has a flame shape corresponding with flame variation B and record the height observed to the nearest 0.5 mm when using the manual apparatus 100.

When using the testing apparatus 200, the software of the computer 204 analyses images of the flame F taken by the digital camera 202 and automatically detects when the flame F has a flame shape corresponding with flame variation B, and then the automated apparatus 200 determines the height $L''$ of that flame F to the nearest 0.1 mm and records the value the height $L''$. The digital camera 202 viewing at the flame F through a window that may include a filter such as an anti-infrared filter between the flame and the digital camera.

As mentioned above, the ASTM D1322-19 test procedure calls for three separate observations of flame height ($L^1$, $L^2$, $L^3$) at the smoke point by repeating the flame appearance sequence specified in Section 11.5 of the ASTM D1322-19 test procedure. These observations or readings are then averaged together to calculate the average reading "L".

According to ASTM D1322-19 the final smoke point is calculated (to the nearest 0.1 mm) via equation (2) from ASTM D1322-19 Section 12, which is "Smoke Point=L×f." In this equation, "L" is equal to the average of three individual readings or observations of flame height $L''$, and "f" is the correction factor (sometimes referred to as the lamp factor). As described above, the correction factor "f" is calculated consistent with Section 10 of the ASTM D1322-19 test procedure (i.e., step ii) before performing the test procedure (step iii).

However, in the present invention the smoke point is typically calculated (to the nearest 0.1 mm), via a modified approach using equation (2) from ASTM D1322-19, but also correcting for humidity with a humidity correction factor $f_h$ and optionally correcting for pressure with a pressure correction factor $f_p$. The device calibration, to determine the correction factor "f" to account for errors related to the camera itself used for measuring smoke point such as camera or lens faults or adjustment tolerances, is more accurate because it is calibrated using smoke point values corrected for humidity and preferably also pressure.

When using the testing apparatus 200, the digital camera 202, the computer 204 with its associated software, and the displacement system 106 work together to read and record the three separate observations of flame height at the smoke point per Section 11.6 of the ASTM D1322-19 test method. The computer 204 automatically averages the three readings or observations of flame height $L^1$, $L^2$, $L^3$ to compute the average reading "L" and then calculates smoke point by multiplying the average reading "L" by the correction factor "$f_h$," which is the humidity correction factor. The computer 204 optionally also calculates "$f_p$," which is the pressure correction factor.

Then, the result of the equation may be reported as the smoke point of the sample tested and rounded to the nearest 0.1 mm pursuant to Section 13 of the test method (i.e., step v).

Rather than correct the average measured flame height, the test apparatus 200 may correct each observed flame height $L''$ as a function of the value of AH (absolute humidity). As previously mentioned, the test method directs the test operator to make three separate observations of flame height at smoke point, and it has been observed increasing AH correspondingly results in decreasing smoke point values. Thus, the humidity correction may be applied in real time to correct each of the three observations of flame height. In particular, the computer 204 may multiply each observation of flame height $L''$ by the humidity correction before calculate the average reading L.

Figure 5A:
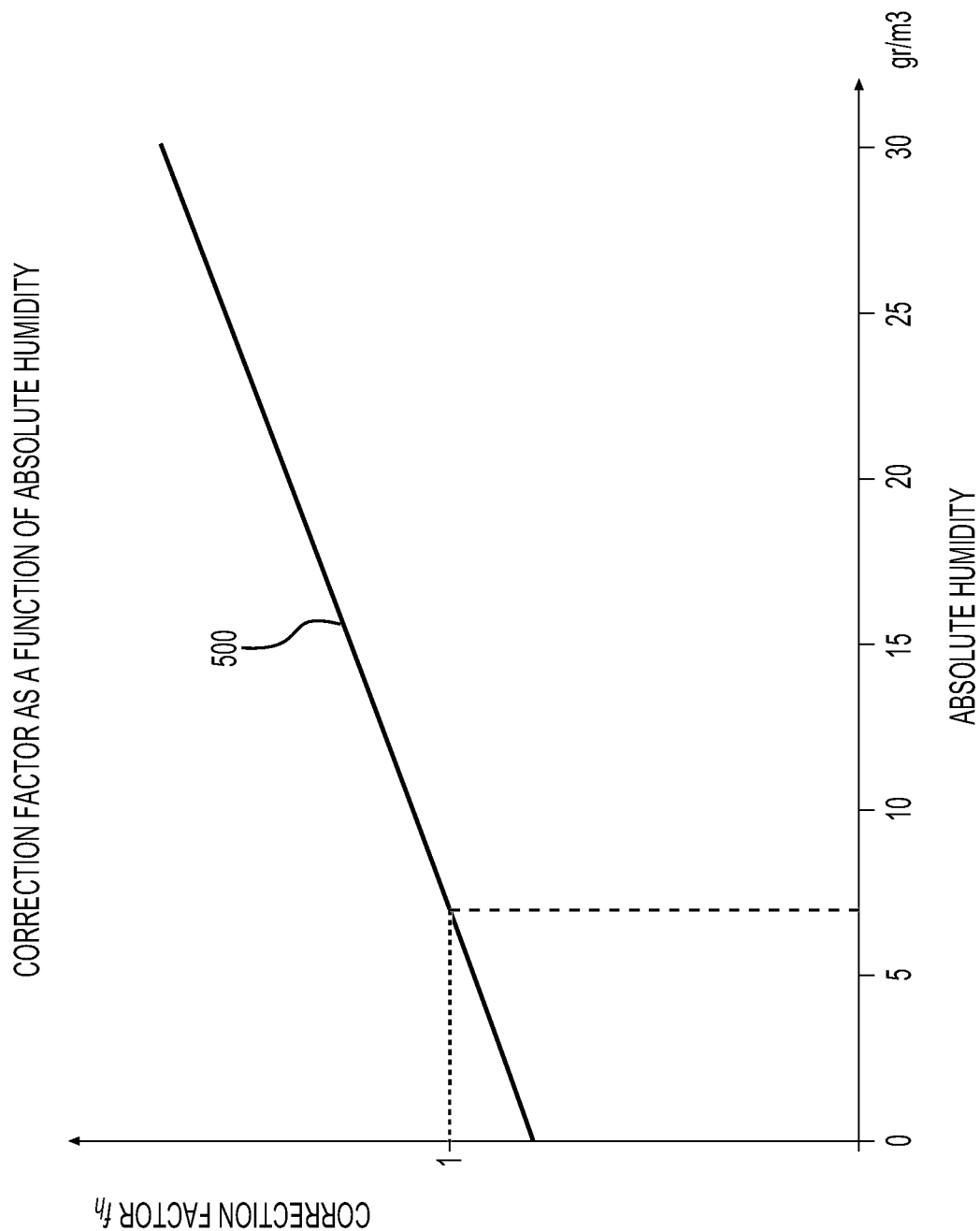
FIG. 5A is a plot of a humidity-based correction factor $f_h$ versus absolute humidity.

FIG. 5A is a plot of the humidity correction factor $f_h$ as a function of absolute humidity (AH), according to one or more embodiments of the present disclosure. In this plot, the reference values defined were obtained at an absolute humidity of 7 gr/m$^3$, which corresponds to 40.4% RH at 20° C. Here, a curve 500 has been derived that specifies a particular value for the humidity correction factor $f_h$ based on the particular absolute humidity (AH) represented on the X-axis in the plot. As seen on FIG. 5A correction factor $f_h$ is 1 at the normalized value of AH of 7 gr/m$^3$. The computer 204 may store the curve 500 (or one or more similar to it) in a memory of the computer 204 so that the computer 204 may identify the humidity correction factor $f_h$ corresponding to the actual humidity (AH) encountered during a particular use of the testing apparatus 200, which is calculable using data measured via one or more sensors. The computer 204 may then multiply each of the observed flame heights $L''$ (i.e., $L^1$, $L^2$, $L^3$) by the humidity correction factor $f_h$ such that each of the three separate flame height observations $L^1$, $L^2$, $L^3$ will account for the impact of humidity on flame height (i.e., humidity corrected flame height observations $f_h*L^1$, $f_h*L^2$, $f_h*L^3$). The three flame height observations that have been corrected based on humidity $f_h*L^1$, $f_h*L^2$, $f_h*L^3$ may be averaged together to obtain the average reading L. Thus, the average reading L may be obtained using the following Equation (3):

$$L = (f_h * L^1 + f_h * L^2 + f_h * L^3)/3 \quad (3)$$

Figure 5B:
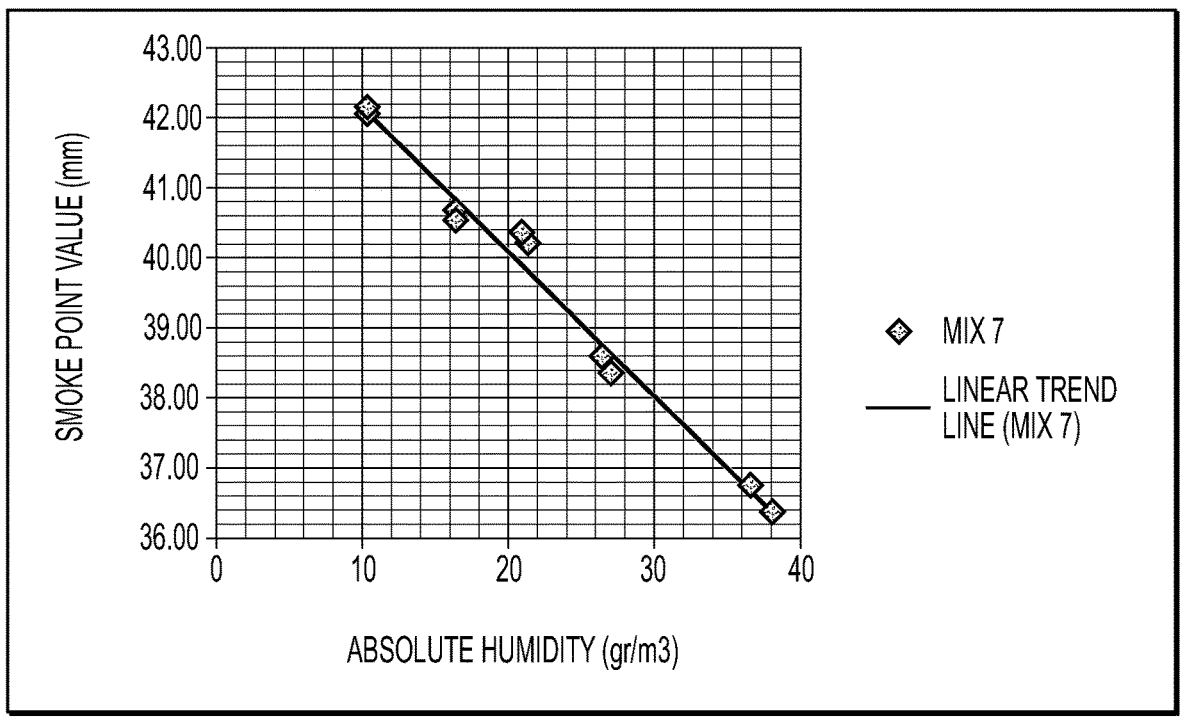
FIGS. 5B-5C are exemplary smoke point measurements utilized to deduce the humidity based correction factor $f_h$; these graphs are examples of several measurements (represented by the dots) at different absolute humidities wherein the lines respectively plotted in the FIGS. 5B and 5C are the trend curves calculated by EXCEL and used to show the linearity of the influence, thus these lines are not the humidity correction factor $f_h$ discussed elsewhere in the specification.
Figure 5C:
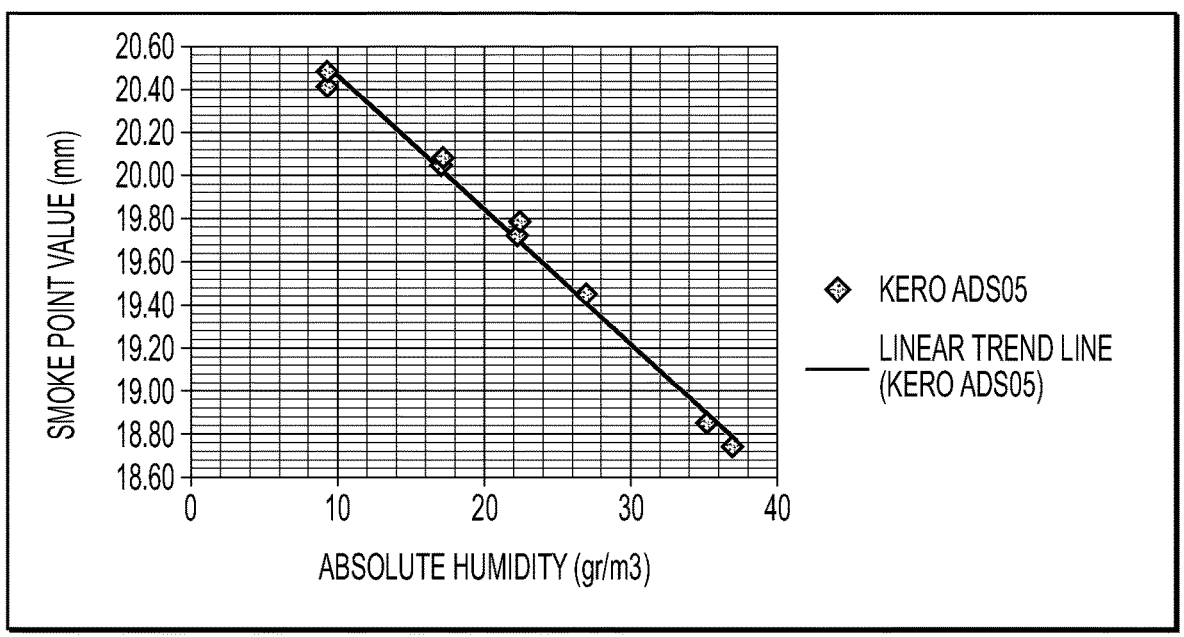

The curve 500 in FIG. 5A is the humidity correction curve as a function of absolute humidity AH. The curve 500 was established by carrying out various smoke point measurements under different humidity conditions, for example, in a room or testing environment suitable for modulating humidity and temperature. The various smoke point measurements were carried out on the seven reference fuel blends specified in Section 7.4 (i.e., mix 1 to mix 7) and on several kerosene samples, using the procedure specified in Section 11. These various smoke point measurements allow the humidity correction factor $f_h$ to be deduced as a function of the absolute humidity (AH) and the measured flame height. FIGS. 5B and 5C are plots of data points, and plotted lines through the data points, for testing data illustrating smoke point measurement tests carried out on ASTM D1322-19 Mix 7 and on a kerosene (Kero ADS05). These plots of this testing data were utilized to establish a formula for the humidity correction factor $f_h$ as a function of the absolute humidity (AH) and the measured flame height. These graphs are examples of several measurements (represented by the dots) at different absolute humidities. The plotted lines of FIGS. 5B and 5C are each the trend curve (linear tread line) calculated by EXCEL and used to show the linearity of the influence. This line is not the correction factor $f_h$. With this and other experimental and testing data, an empirical formula for calculating the humidity correction factor $f_h$ may be established. In particular, the humidity correction factor $f_h$ may calculated by the following Equation (4):

$$f_h = 1 + (H_m * ((AH * K_a) - K_b)) \quad (4)$$

where:
$H_m$ is the measured flame height,
AH is the absolute humidity, and
and $f_h$ is the humidity correction factor.
The empirical formula was obtained from a large quantity of measurement (FIGS. 5B and 5C represent a part of it) in which all the correction points were plotted on an EXCEL graph, a line joining these points was then calculated and $K_a$ and $K_b$ are the constant values describing this line (equation of type a*x+b) which can be developed by applying linear regression or other suitable analysis to the empirical data, for example in FIGS. 5B and 5C, obtained from trials with reference materials in which only AH is varied.

Thereafter, the final smoke point result may be obtained by multiplying the average reading L of flame height, which has been corrected based on humidity, by the lamp factor f.

Ways to Apply a cCrrection Based on the Pressure

Thus, the ASTM D1322-19 test procedure calls for three separate observations of flame height ($L^1$, $L^2$, $L^3$) at the smoke point by repeating the flame appearance sequence specified in Section 11.5 of the ASTM D1322-19 test procedure. These observations or readings are then averaged together to calculate the average reading "L", and then the average reading "L" is multiplied by the correction factor "f" (lamp factor) to correct for ambient pressure and obtain the final smoke point.

As mentioned above, measurement of the flame height L" recorded during a calibration may incorporates several biases from various sources. Bias may result from the testing equipment itself and/or from other ambient consideration. For example, a bias may result from the error of the flame height L" measurement itself and possible defects in the optics of the camera 202. In some cases, this bias may be quite small such that it could be considered as a constant.

As mentioned above, atmospheric pressure is another atmospheric condition that impacts smoke point measurements. In particular, the smoke point value decreases when the atmospheric pressure increases.

As discussed above an operator typically performs an initial calibration to obtain the correction factor "f" of the ASTM D1322-19. However, the present invention in its preferred aspects employs a pressure correction factor "$f_p$" to avoid the need to recalibrate if the pressure difference between the pressure at initial calibration as opposed to the current measurement pressure is greater than +/−0.7 kPa (either more than 0.7 kPa below or more than 0.7 kPa above). ASTM D1322-19 records pressure during calibration when calculating lamp factor "f" and when making a current measurement. ASTM D1322-19 also requires recalibration if the pressure difference between the pressure at calibration as opposed to the current measurement pressure is greater than +/−0.7 kPa.

The correction factor "f" of the ASTM D1322-19 test method is calculated from measurements made on reference fuel blends (or mixes), as specified in Section 7.4 and Table 1 of the ASTM D1322-19 test method, under identical pressure conditions (within ±0.7 kPa). Table 1 of the ASTM D1322-19 test method identifies seven different reference fuel blends (i.e., mix 1, mix 2, mix 3, mix 4, mix 5, mix 6, and mix 7), each comprising different mixtures of toluene and isooctane (in % V/V), and further provides a standard smoke point (at 101.3 kPa) for each of the seven different reference fuel blends. The test operator must select the two reference fuel blends whose values frame (brackets) the value measured on the fuel sample to be tested. The calibration values of the seven different reference fuel blends may be incorporated in the calibration database stored in the memory of the computer 204. However, as discussed above, the test method requires a new calibration of the testing apparatus if the pressure has varied by more than 0.7 kPa (i.e., ±0.7 kPa) at the time of the manual test method (see Section 10.1), or if there are no calibration values saved in the calibration database within 0.7 kPa of atmospheric pressure at the time of the automated test method (see Section 10.2.2).

For example, before performing the test method, the test operator records the barometric pressure and checks the calibration database for calibration values associated with the recorded pressure or within ±0.7 kPa thereof. If the calibration values exist at the recorded pressure ±0.7 kPa, the test operator could perform the test method and the automated apparatus will select the two calibration values bracketing the smoke point of tested sample. However, if no calibration values exist for the seven blends (mix 1 to mix 7) in the calibration database at the recorded pressure ±0.7 kPa, the test method instructs the operator to perform a new calibration at the recorded pressure, which is time consuming and inconvenient considering the often busy schedules of laboratories. Thus, test operators confronted with the instruction to perform a new calibration will simply enter (use) a barometric pressure for which the calibration values exist, rather than using values corresponding with the actual pressure, which in turn generates a biased result.

The invention also provides devices and methods which improve upon accounting for pressure as in ASTM D1322-19 by providing an additional correction for humidity by employing the humidity correction factor $f_h$. In this case lamp factor f is calculated from flame heights corrected for humidity according to the equation flame height×$f_h$. In this alternative, the testing apparatus 200 of the invention includes the pressure sensor 216 for measuring the current atmospheric pressure "P" in real time, and the computer 204 may then preferably use this measurement data to apply a correction based on pressure (i.e., a pressure-based correction "$f_p$") when performing the smoke point calculations. Also, although there is an initial calibration per ASTM D1322-19 this improved method avoids having to redo (or to have done previously and stored) calibrations for every time the pressure varied more than ±0.7 kPa, to determine the correction factor "f". Also, this correction factor "f", to account for errors related to the camera itself used for measuring smoke point such as camera or lens faults or adjustment tolerances, is more accurate because it is calibrated using smoke point values corrected for humidity and pressure.

The pressure-based correction "$f_p$" may be applied in two different ways. The test apparatus 200 may be configured to perform either pressure-based correction as selected by the test operator.

In the first method, the test operator may choose to apply the pressure-based correction in real-time to each of the three observed flame height $L^n$ measurements, similar as described above with respect to the application of the humidity based correction. Thus, each of the three flame height observations $L^1$, $L^2$, $L^3$ may be multiplied by the pressure-based correction "$f_p$", and then averaged together to obtain the average measurement L. Thus, the average reading L corrected for pressure may be obtained using the following Equation (5):

$$L = (f_p * L^1 + f_p * L^2 + f_p * L^3)/3 \tag{5}$$

Thereafter, the final smoke point result may be obtained by multiplying the average reading L of flame height, which has been corrected based on pressure, by the lamp factor f.

The first method of applying the pressure-based correction involves a real-time correction to the flame height measurement in a similar manner as with the application of the humidity-based correction. Here, each flame height measurement is corrected to obtain the height at a normalized pressure, for example, at 1013 hPa. The calibrations with mixtures therefore record the reference values for that particular normalized pressure (e.g., 1013 hPa). In this manner, the calibrations therefore only include the intrinsic bias to the testing apparatus 200 (e.g., optics defects). Then, during the normal test method on a kerosene sample, the flame height $L^n$ is also corrected in real time as a function of the pressure, the result therefore being measurements equivalent to the normalized pressure (e.g., 1013 hPa). The correction calculation according to the lamp factor "f" described in the ASTM D1322-19 test method therefore uses the calibrations with the values at the normalized pressure (e.g., 1013 hPa). Here, a single calibration set with the 7 mixes may be utilized, without the need to do any more.

Figure 6:
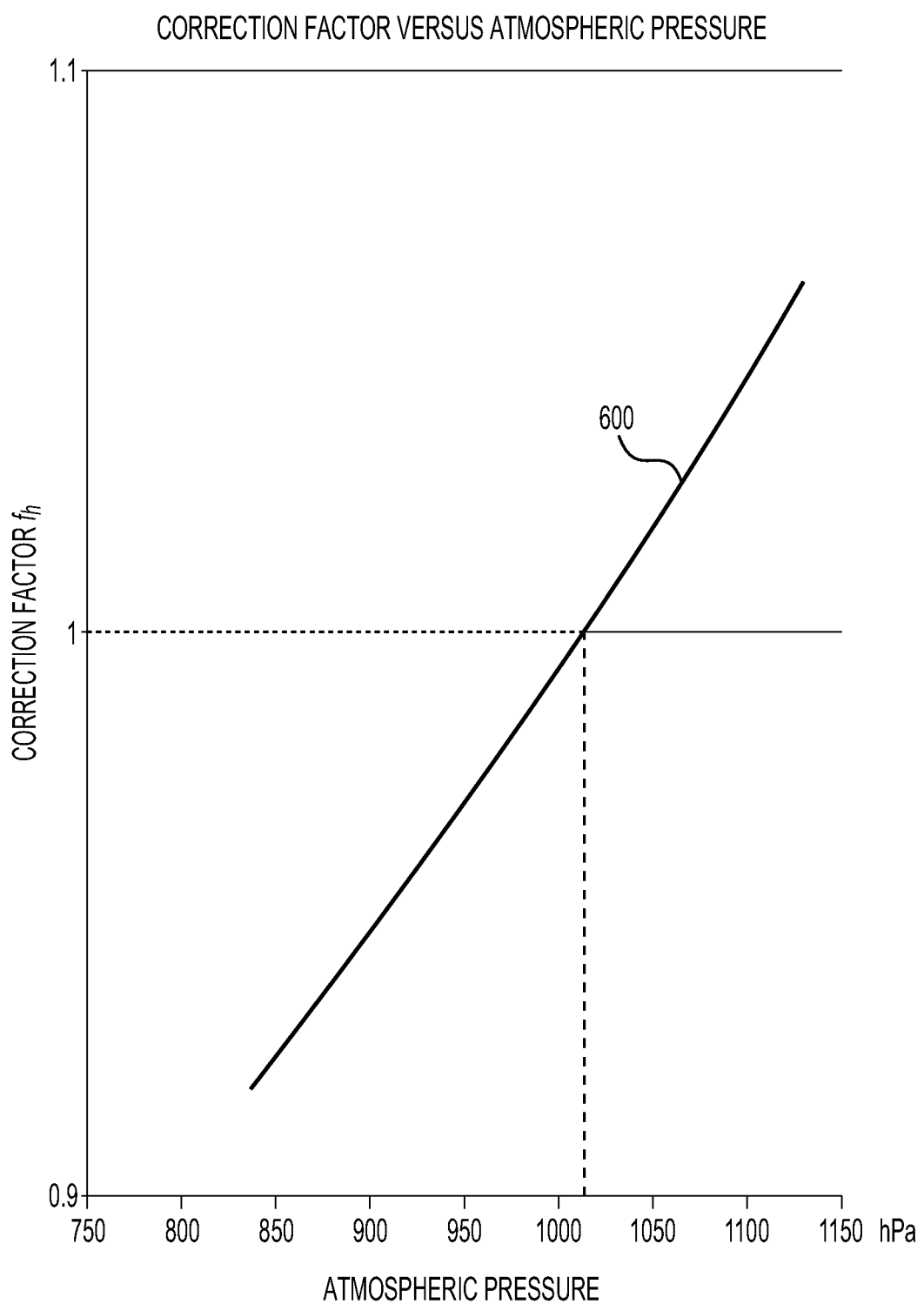
FIG. 6 is a plot of atmospheric pressure-based correction factor versus atmospheric pressure.

FIG. 6 is a plot of correction factor versus atmospheric pressure which shows the atmospheric pressure correction factor "$f_p$" as a function of atmospheric pressure (P) in hectopascals (hPa), according to one or more embodiments of the present disclosure. In this plot, the atmospheric pressure correction factor is equal to 1 for a pressure of 1013 hPa, such that the reference values are defined by the standard testing method at this pressure. This plot shows a derived curve 600 that specifies a particular value for the pressure correction factor "$f_p$" based on the particular atmospheric pressure (P) represented on the X-axis in the plot. The curve 600 (or one similar to it) may be saved within the computer 204, so that the computer 204 can identify the pressure-based correction factor "$f_p$" corresponding to the actual pressure "P" encountered during a particular use of the testing apparatus and measured via the pressure sensor 216. Then the computer multiplies that pressure-based correction factor "$f_p$" against each of the observed flame heights $L^n$ such that each of the three separate flame height observations (i.e., $L^1$, $L^2$, $L^3$) account for the impact of atmospheric pressure on flame height. Thus, each of the three flame height observations $L^1$, $L^2$, $L^3$ may be multiplied by the pressure-based correction "$f_p$", and then averaged together to obtain the average measurement L. The average reading L may be obtained using the following Equation (5):

$$L = (f_p * L^1 + f_p * L^2 + f_p * L^3)/3 \tag{5}$$

Thereafter, the average reading "L" is multiplied by the lamp factor "f" to obtain the final smoke point via Equation (2) described above. Similar to development of a plot for $f_h$ a plot for $f_p$, such as FIG. 6, can be developed by applying linear regression or other suitable analysis to empirical data obtained from trials with reference materials in which only pressure is varied.

Figure 7A:
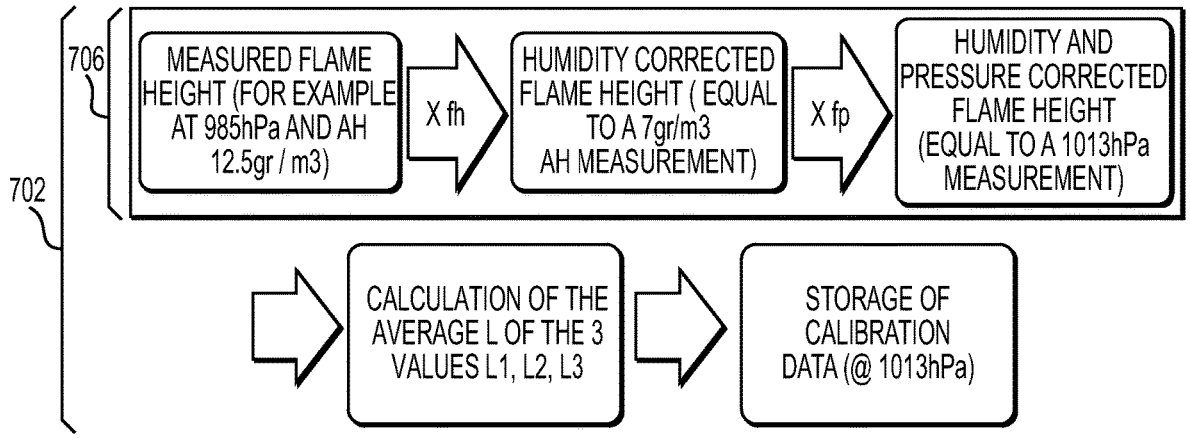
FIG. 7A illustrates an exemplary calibration measurement with a pressure correction method 1 that may be incorporated into a smoke point test method, according to the present disclosure.
Figure 7B:
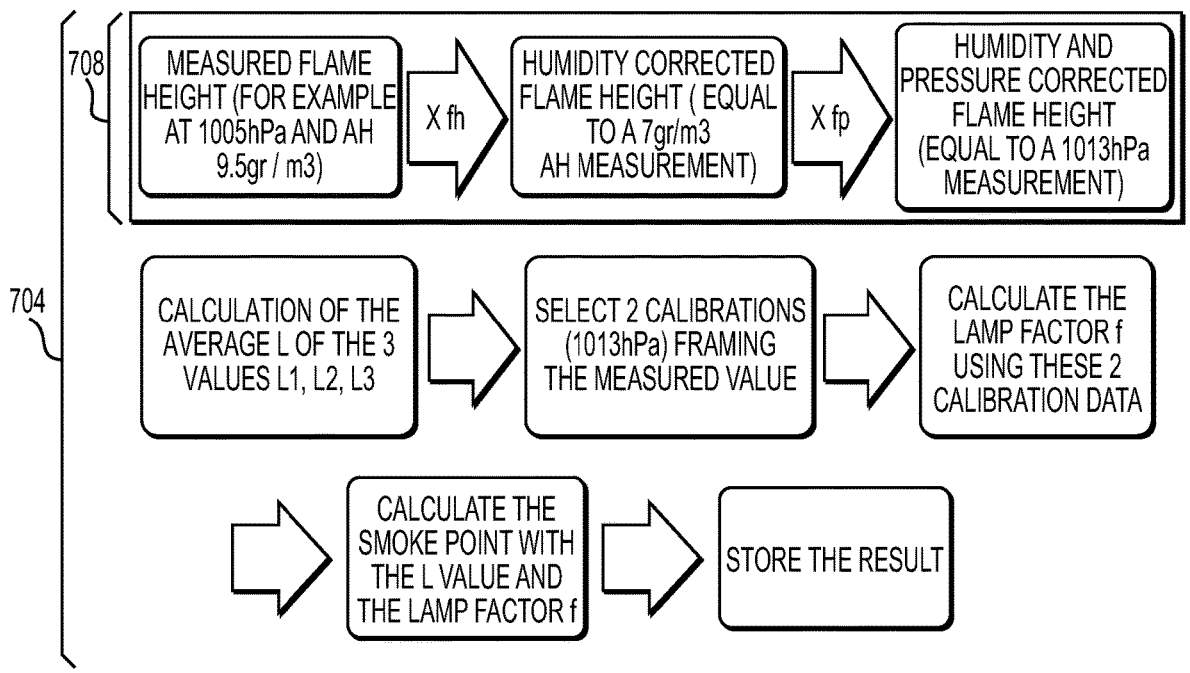
FIG. 7B illustrates an exemplary test measurement with the pressure correction method 1.

FIGS. 7A and 7B illustrate an exemplary process of conducting a first method of applying the humidity-based correction, the pressure-based correction, and the lamp factor for calibration measurement and test measurement with pressure correction method 1. FIG. 7A shows calibration measurement with pressure correction method 1. The method has one calibration per reference mixture, i.e. 7 calibrations. FIG. 7A shows the process may generally include a calibration measurement with pressure correction method 1 comprising a first segment 702, where calibration measurements are conducted or performed (i.e., the calibration measurement segment 702). This shows a first set of calibration steps 706 comprising measuring flame height (for example at 985 hPa and AH 12.5 g/m$^3$) and multiplying this measuring flame height by humidity correction factor $f_h$ to calculate humidity corrected flame height (for example equal to a 7 gr/m$^3$ AH measurement). Then multiplying this value by pressure correction factor $f_p$ to calculate humidity and pressure corrected flame height (for example at pressure equal to a 1013 hPa pressure measurement). In the illustrated example, the calibration measurement segment 702 is performed for each of the seven reference fuel blend mixtures, such that seven calibrations are performed. Thus, the calibration measurement segment 702 is performed seven separate times, once with each of the seven reference fuel blend mixtures. The first set of calibration steps 706 relating to measuring the flame height $L^n$ is performed three separate times to thereby obtain three separate observations of flame height ($L^1$, $L^2$, $L^3$). In the illustrated example, the first set of calibration steps 706 also includes multiplying each measured flame height $L^n$ by the humidity correction factor $f_H$ and then multiplying that resulting product by the pressure-based correction $f_p$ (i.e., $L^n * f_h * f_p$). Thus, the first set of calibration steps 706 yields three flame height measurements that have each been corrected based on humidity and pressure (i.e., humidity and pressure corrected flame height measurements: $L^1*f_h*f_p$; $L^2*f_h*f_p$; $L^3*f_h*f_p$). The calibration measurement segment 702 then includes calculating the average reading L from the three humidity and pressure corrected flame height measurement (i.e., $L=[(L^1*f_h*f_p)+(L^2*f_h*f_p)+(L^3*f_h*f_p)]/3$). Then, the calibration measurement segment 702 includes storing or saving this calibration data in the memory of the computer 204 and/or in a calibration database.

FIG. 7B shows a test measurement with pressure correction method 1 comprising a second segment 704, where test measurements are conducted or performed (i.e., test measurement segment 704). Thereafter, as shown in FIG. 7B, the test sample may be measured pursuant to the test measurement segment 704. The test measurement segment 704 includes a set of testing steps 708 associated with making observations of flame height (i.e., measuring flame height $L''$), and this first set of testing steps 708 is performed three separate times to obtain three separate observations of flame height ($L^1$, $L^2$, $L^3$). In the illustrated example, the set of testing steps 708 also includes multiplying each measured flame height $L''$ by the humidity correction factor $f_h$ and then multiplying that resulting product by the pressure-based correction $f_p$ (i.e., $L''*f_h*f_p$). Thus, the first set of testing steps 708 yields three flame height measurements that have been corrected based on humidity and pressure (i.e., humidity and pressure corrected flame height measurements: $L^1*f_h*f_p$; $L^2*f_h*f_p$; $L^3*f_h*f_p$). The test measurement segment 704 then includes calculating the average reading L from the three humidity and pressure corrected flame height measurements (i.e., $L=[(L^1*f_h*f_p)+(L^2*f_h*f_p)+(L^3*f_h*f_p)]/3$). Then, the test operator or computer 204 may select the two calibrations that frame (or bracket) the average reading L and then use Equation (1) to calculate the lamp correction factor "f" using the foregoing two calibrations bracketing/framing the measured value. Thereafter, the test operator or computer 204 may calculate the final smoke point via Equation (2) (i.e., smoke point=L*f) and then the final result for smoke point may be stored in the memory of the computer 204 and/or reported.

It should be noted that, while the process exemplified in FIGS. 7A-B corrects based on humidity and pressure, in other examples, the pressure-based correction may be utilized without performing the humidity based correction.

Alternatively, in a second method the test operator may choose to apply the pressure-based correction to the calibration measurement result at some normalized pressure value (e.g., 1013 hPa (hectopascal)) such that the lamp factor correction factor "f" resulting from the calibration measurement includes the pressure correction, rather than being applied to the flame height measurements. Thus, error in flame height measurements may be corrected during the calibrations to obtain a set of calibration values for each of the seven different reference fuel blends at a given pressure. Then during the normal test on a test sample (e.g., kerosene), the measured height is not in this second case corrected according to the pressure, but the calibration values necessary to calculate the lamp factor, are calculated by correcting the values recorded at 101.3 KPa as a function of the pressure value measured during the test.

Figure 8A:
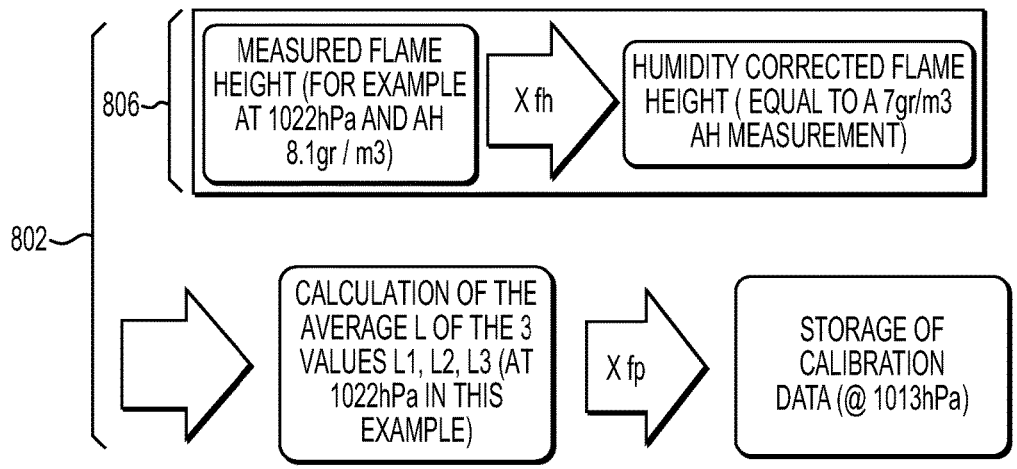
FIG. 8A illustrates an exemplary calibration measurement with a pressure correction method 2 that may be incorporated into a smoke point test method, according to the present disclosure.
Figure 8B:
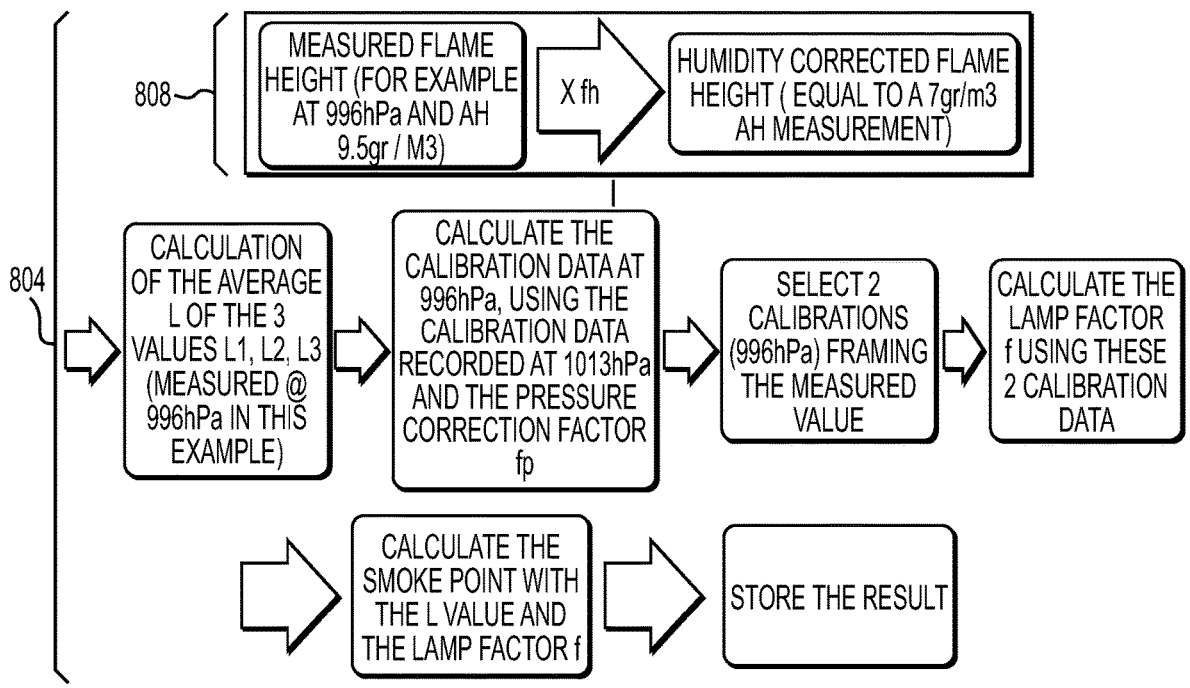
FIG. 8B illustrates an exemplary test measurement with the pressure correction method 2.

FIGS. 8A and 8B illustrate an exemplary process of conducting the alternative second method of applying the humidity-based correction, the pressure-based correction, and the lamp factor for calibration measurement and test measurement with pressure correction method 2. FIG. 8A shows calibration measurement with pressure correction method 2. The method has one calibration per reference mixture, i.e. 7 calibrations. FIG. 8B shows a test measurement with pressure correction method 2. As seen in FIG. 8A, this second method of applying the pressure-based correction involves applying the humidity-based correction $f_h$ and pressure-based correction $f_p$ on the calibration values utilized to calculate the lamp correction factor "f". As seen in FIG. 8B this is thereafter multiplied by the average reading "L" to obtain the final smoke point. Here, no pressure-based correction is applied to the individual flame height measurements $L''$ during tests and calibrations. Rather, the pressure-based correction $f_p$ is applied to the calibration measurement average result to obtain the value at a normalized pressure, for example, at 1013 hPa. The method therefore uses the stored calibrations with the values at the normalized pressure (e.g., 1013 hPa). The test is carried out at the current ambient pressure and the smoke point measurements are therefore carried out at this pressure. For calculation of the lamp factor "f", the calibration values must be within ±0.7 kPa of the current pressure. The system generates the calibration values at the necessary pressure (that of the test pressure), taking as a basis the calibrations recorded for 1013 hPa, and applying a correction corresponding to the pressure difference. The two calculated calibration values bracketing (or framing) the flame measurement of the test sample are selected and then used in Equation (1) to calculate the lamp factor "f", which may then be multiplied by the average reading L to generate the final smoke point, as described in Equation (2), and then the final result may be reported.

The second method of applying the pressure-based correction is therefore identical to the standard test method, except that calibrations calculated from those stored and normalized at 1013 hPa are used, instead of calibration carried out specifically at the desired pressure, as exemplified in FIG. 8A.

In particular, calibration values recorded for 1013 hPa are divided by the pressure correction factor corresponding to the pressure measured during the test, such that the calibration values for the test pressure are obtained. The two calibration values that bracket or frame the flame measurement of the test sample are selected and are used as in the ASTM Standard to calculate the lamp factor f via Equation (1). For example, error in flame height measurements may be corrected during the calibrations to obtain a set of calibration values for each of the seven different reference fuel blends at a given pressure. Then, when performing the test method on the test sample (e.g., kerosene), the measured height $L''$ is not in this second method corrected according to the pressure (though, the measured heights $L''$ may each be corrected for humidity by multiplying each by the humidity correction factor $f_h$ before averaging them to obtain the average reading L), but the calibration values necessary to calculate the lamp factor f are calculated by correcting the values recorded at 101.3 kPa as a function of the pressure value measured during the test.

FIG. 8A illustrates an exemplary process of a calibration measurement with pressure correction method 2 for conducting the second method of applying the pressure-based correction. As shown, the process may generally include a first segment 802, where calibration measurements are conducted or performed (i.e., the calibration measurement segment 802). FIG. 8B illustrates a second segment 804, where test measurements are conducted or performed (i.e., test measurement segment 804).

In FIG. 8A, the calibration measurement segment 802 is performed for each of the seven reference fuel blend mixtures, such that seven calibrations are performed. In other words, the calibration measurement segment 802 is performed seven separate times, once with each of the seven reference fuel blend mixtures. The calibration measurement segment 802 includes a first set of calibration steps 806 comprising measuring flame height (for example at 1022 hPa and AH 8.1 g/m3). The first set of calibration steps 806 is performed three separate times to thereby obtain three separate observations of flame height ($L^1$, $L^2$, $L^3$). The first set of calibration steps 806 then includes a step of generating humidity corrected flame height measurements, wherein each of the flame height measurements ($L^1$, $L^2$, $L^3$) is corrected based on humidity by multiplying each measured flame height by humidity correction factor $f_h$ to calculate humidity corrected flame height (for example equal to a 7 gr/m3 AH measurement). Here, for example, the first set of calibration steps 806 thus includes multiplying each measured flame height $L''$ by the humidity correction factor $f_h$ (i.e., $L''*f_h$), such that the first set of calibration steps 806 yields three flame height measurements that have been corrected based on humidity (i.e., humidity corrected flame height measurements: $L^1*f_h$; $L^2*f_h$; $L^3*f_h$). The calibration measurement segment 802 then includes calculating the average reading L of the humidity corrected flame height measurements (i.e., $L=[(L^1*f_h)+(L^2*f_h)+L^3*f_h)]/3$). Then, the calibration measurement segment 802 includes storing or saving this calibration data in the memory of the computer 204 and/or in a calibration database.

The process exemplified in FIGS. 8A-8B corrects based on humidity and pressure, but in other examples, the pressure-based correction may be utilized without performing the humidity-based correction.

Thereafter, as seen in FIG. 8B the test sample may be measured pursuant to the test measurement segment 804. The test measurement segment 804 includes a first set of testing steps 808 associated with making observations of flame height (i.e., measuring flame height $L''$), and this first set of testing steps 808 is performed three times to obtain three separate observations of flame height ($L^1$, $L^2$, $L^3$) that may be averaged together to obtain the average reading L. In the illustrated example, the first set of testing steps 808 also includes multiplying each measured flame height $L''$ by the humidity correction factor $f_h$ (i.e., $L''*f_h$). Thus, the first set of testing steps 808 yields three flame height measurements that have been corrected based on humidity (i.e., humidity corrected flame height measurements: $L^1*f_h$; $L^2*f_h$; $L^3*f_h$). The test measurement segment 804 then includes calculating the average reading L from the three humidity corrected flame height measurement (i.e., $L=[(L^1*f_h)+(L^2*f_h)+(L^3*f_h)]/3$). Then, the test operator or the computer 204 may calculate the calibration data at ambient pressure (e.g., 996 hPa), using the calibration data recorded at normalized pressure (e.g., 1013 hPa) and the pressure-based correction $f_p$. In particular, the calibration data is calculated during the test measurement segment 804 by dividing the calibration data recorded during the calibration measurement segment 802 by the pressure-based correction $f_p$. Then, the test operator or computer 204 may select the two calibrations that frame (or bracket) the average reading L (of the three humidity corrected flame height measurements) and then use Equation (1) to calculate the lamp correction factor "f" using the foregoing two calibrations bracketing/framing the measured value. Thereafter, the test operator or computer 204 may calculate the final smoke point via Equation (2) (i.e., smoke point=L*f) and then the final result for smoke point may be stored in the memory of the computer 204 and/or reported.

Accordingly, under either of the foregoing two methods, it is no longer necessary to make more than a single calibration batch with the seven different reference fuel blends, and the constraint of recalibrating each time the pressure varies by more than +/−0.7 kPa disappears, which further simplifies and facilitates performance of the test method.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein.

PARTICULAR EMBODIMENTS OF THE INVENTION

The following paragraphs present particular embodiments of the present invention Paragraph A. The invention provides a testing device for determining smoke point of a hydrocarbon, comprising:
  an apparatus for determining the smoke point conforming to the specifications of an ASTM D1322-19 standard,
  means for taking a series of digital images of a flame;
  an ambient relative humidity sensor for measuring relative humidity;
  an ambient temperature sensor for measuring temperature;
  a computer system linked to the means for taking the series of digital images of a flame, linked to the humidity sensor, and linked to the temperature sensor, the computer system programmed to enable digital images taken by the means for taking a series of digital images to be analyzed to measure flame height, and for using temperature measured by the ambient temperature sensor in combination with relative humidity measured during testing by the relative humidity sensor to calculate the absolute humidity and to correct the measured flame height as a function of a difference between the calculated absolute humidity and a normalized absolute humidity value.

The testing device of paragraph A may include any of the following modifications.

The testing device of Paragraph A, may further comprise an ambient pressure sensor linked to the computer system, wherein the computer system corrects measured flame point values of the hydrocarbon as a function of a difference between a current ambient pressure measured by the pressure sensor during testing and a normalized pressure value.

In the testing device of Paragraph A, the ambient temperature sensor may be part of the ambient relative humidity sensor or a separate from the ambient relative humidity sensor.

The testing device of Paragraph A, may further comprise an ambient pressure sensor linked to the computer system, wherein the computer system corrects measured flame point values of the hydrocarbon based on ambient pressure measured by the ambient pressure sensor.

In the testing device of Paragraph A, the means for taking a series of digital images of the flame may comprise a digital camera.

The testing device of Paragraph A, may further comprise an anti-infrared filter placed between the an apparatus for determining the smoke point conforming to the specifications of an ASTM D1322-19 standard and the means for taking the series of digital images.

In the testing device of Paragraph A, the normalized humidity value may be a value in a range of 0 gr/m$^3$ to 40 gr/m$^3$, preferably 7 gr/m$^3$.

In the testing device of Paragraph A, the means for taking a series of digital images of a flame may comprise a digital camera;
wherein the apparatus for determining the smoke point conforming to the specifications of an ASTM D1322-19 standard comprises a candle for holding a wick, a graduated scale against which to measure flame height, a gallery configured through which to take the digital images of the flame and the graduated scale, a candle displacement system for adjusting height of a flame from the wick of the candle.

The testing device of Paragraph A, may further comprise:
a power supply, and
a housing for containing:
the digital camera,
the ambient relative humidity sensor,
the ambient temperature sensor, and
the computer system linked to the means for taking the series of digital images, wherein the computer system comprises electronics comprising a microprocessor.

In the testing device of Paragraph A, the testing device may comprise means for ventilation, an air intake vent for admitting air flow to the test apparatus housing and an air exhaust vent for discharging out of the housing air flow that has been heated within the test apparatus housing.

In the testing device of Paragraph A, the ambient temperature sensor may be part of the ambient relative humidity sensor or a separate from the ambient relative humidity sensor, wherein the computer system corrects measured heights of the flame as a function of a difference between a current ambient pressure measured by the ambient pressure sensor during testing and a normalized pressure value.

In the testing device of Paragraph A, the means for taking a series of digital images of a flame may comprise a digital camera;
wherein the apparatus for determining the smoke point conforming to the specifications of an ASTM D1322-19 standard comprises a candle for holding a wick, a graduated scale against which to measure flame height, a gallery configured through which to take the digital images of the flame and the graduated scale, a candle displacement system for adjusting height of a flame from the wick of the candle,
wherein the normalized pressure value is between 800 and 1100 hPa, preferably 1013 hPa.

In the testing device of Paragraph A, the ambient temperature sensor may be part of the ambient relative humidity sensor or a separate from the ambient relative humidity sensor, wherein the computer system corrects measured heights of the flame based on ambient pressure measured by the integrated ambient pressure sensor as a function of a difference between a current ambient pressure measured by the pressure sensor during testing and a normalized prior ambient pressure recorded during calibration.

In the testing device of Paragraph A, the ambient relative humidity sensor may be configured to also include the temperature sensor to measure temperature.

In the testing device of Paragraph A, the ambient temperature sensor may be part of the ambient relative humidity sensor or a separate from the ambient relative humidity sensor, wherein the computer system corrects measured heights of the flame as a function of a difference between a current ambient pressure measured by the ambient pressure sensor during testing and a normalized pressure value, further comprising a housing having an intake vent and an exhaust vent, wherein the ambient relative humidity sensor is provided proximate to the intake vent.

In the testing device of Paragraph A, the ambient temperature sensor may be part of the ambient relative humidity sensor or a separate from the ambient relative humidity sensor, wherein the computer system corrects measured heights of the flame as a function of a difference between a current ambient pressure measured by the ambient pressure sensor during testing and a normalized pressure value, further comprising a housing having an intake vent and an exhaust vent, wherein the ambient relative humidity sensor is provided proximate to the intake vent, wherein the ambient relative humidity sensor is provided on a chassis of the housing.

In the testing device of Paragraph A, the ambient temperature sensor may be part of the ambient relative humidity sensor or a separate from the ambient relative humidity sensor, wherein the computer system corrects measured heights of the flame as a function of a difference between a current ambient pressure measured by the ambient pressure sensor during testing and a normalized pressure value, further comprising a housing having an intake vent and an exhaust vent, wherein the ambient relative humidity sensor is provided proximate to the intake vent, wherein the ambient relative humidity sensor is provided on a chassis of the housing, wherein the housing has an intake vent and an exhaust vent, wherein the ambient temperature sensor is provided proximate to the intake vent.

Paragraph B. The invention also provides a method of determining smoke point of a hydrocarbon fuel sample, comprising:
measuring ambient relative humidity with an ambient relative humidity sensor,
measuring ambient temperature with an ambient temperature sensor,
testing the fuel sample, said testing comprising:
identifying, among different appearances of a flame according to the position of the burner in a lamp, of a particular appearance of a flame,
reading the height of the flame on a graduated scale,
using means for taking and storing digital images to take and store a series of digital images of the flame at such intervals that are sufficiently close to enable, by analyzing these digital images, the detection of change in the shape of the flame,
measuring height of the flame at a moment of the change of shape of the flame, said height being considered the measured smoke point of the hydrocarbon under test, and
inputting the measured height of the flame and measured ambient relative humidity, and measured ambient temperature to a computer system linked to the means for taking and storing digital images and the ambient relative humidity sensor, and the ambient temperature sensor;

said computer system linked to the means for taking the series of digital images of a flame, linked to the humidity sensor, and linked to the temperature sensor, the computer system analyzing digital images taken by the means for taking a series of digital images to measure flame height, and using temperature measured by the ambient temperature sensor in combination with relative humidity measured by the relative humidity sensor during testing to calculate the absolute humidity and to correct the measured flame height as a function of a difference between the calculated absolute humidity and a normalized absolute humidity value to calculate a corrected smoke point; and reporting the corrected smoke point.

The method of Paragraph B, may include any of the following modifications.

The method of Paragraph B, may determine the smoke point conforming to the specifications of an ASTM D1322-19 standard.

The method of Paragraph B, may further comprise measuring ambient pressure with an ambient pressure sensor linked to the computer system, wherein the computer system corrects measured flame point values of the hydrocarbon based on ambient pressure measured by the pressure ambient sensor as a function of a difference between a current ambient pressure measured by the pressure sensor during testing and a normalized pressure ambient pressure value.

The method of Paragraph B, wherein automatically correcting measured smoke point may comprise correcting calibration values during calibration of the testing apparatus as a function of a difference between current atmospheric pressure measured by the integrated pressure sensor and a normalized standard value, preferably the normalized standard value of pressure is between 800 and 1100 hPa, most preferably 1013 hPa.

The method of Paragraph B, wherein the means for taking and storing digital images may comprise a digital camera, wherein automatically correcting measured smoke point may comprise normalizing in real time flame point measurements made by the digital camera to a standard pressure.

The method of Paragraph B, wherein the means for taking and storing digital images may comprise a digital camera, wherein automatically correcting measured smoke point may comprise normalizing in real time flame point measurements made by the digital camera to a standard pressure, wherein the normalized standard value of pressure is 101.3 kPa.

The method of Paragraph B, may further comprise an integrated ambient pressure sensor linked to the computer system, wherein the computer system corrects measured heights of the flame based on ambient pressure measured by the integrated ambient pressure sensor as a function of a difference between a current ambient pressure measured by the pressure sensor during testing and a prior ambient pressure recorded during calibration.

The method of Paragraph B, wherein the image-taking intervals may be between 0.1 and 2.0 seconds.

The method of Paragraph B, wherein the image-taking intervals may be between 0.5 and 1 second.

The method of Paragraph B, wherein the detection of the change in the shape of the flame may be achieved by measuring the sudden change in the speed of reduction of the Feret diameter of the image of the flame.

The method of Paragraph B, wherein the detection of the change in the shape of the flame may be achieved by measuring the sudden change in the speed of reduction of the Feret diameter of the image of the flame, wherein, to detect the sudden change in the speed of reduction of the Feret diameter, this Feret diameter is measured at an angle $\alpha$ less than 45°.

The method of Paragraph B, wherein the detection of the change in the shape of the flame may be achieved by measuring the sudden change in the speed of reduction of the Feret diameter of the image of the flame, wherein the height of the flame is equal to the Feret diameter for $\alpha=0°$ of the image of the flame.

The method of Paragraph B, wherein the detection of the change in the shape of the flame may be achieved by measuring the sudden change in the speed of reduction of the Feret diameter of the image of the flame, wherein the digital image corresponding to the sudden change in the speed of reduction of the Feret diameter is subjected to a thresholding operation (also known as a binarization operation) wherein the thresholding comprises setting to zero all the pixels having a gray level less than the determined threshold and to 1 all the pixels having a value above the threshold, using a determined threshold with the help of one or more standard fuel mixtures (toluene/2,2,4-trimethylpentane) with known smoke point (ASTM D1322-19), wherein the threshold that gives the absolute height of the flame leading to the measured smoke point of the fuel under test is determined with one or more standard fuel mixtures (toluene/2,2,4-trimethylpropane), for which ASTM D1322-19 standard indicates the smoke point.

The method of Paragraph B, wherein the means for taking and storing digital images may comprise a charge-coupled device (CCD) digital camera, complementary metal-oxide-semiconductor (CMOS) image sensor or other imaging sensor, which preferably covers wavelengths ranging from the ultraviolet to the infrared.

The method of Paragraph B, wherein the means for taking and storing digital images may comprise a charge-coupled device (CCD) digital camera, complementary metal-oxide-semiconductor (CMOS) image sensor or other imaging sensor, which preferably covers wavelengths ranging from the ultraviolet to the infrared, wherein an anti-infrared filter may be placed between the flame and the means for taking and storing digital images.

The method of Paragraph B, wherein the means for taking and storing digital images may comprise a charge-coupled device (CCD) digital camera, complementary metal-oxide-semiconductor (CMOS) image sensor or other imaging sensor, which preferably covers wavelengths ranging from the ultraviolet to the infrared, wherein the means for taking and storing digital images may store digital images with at least 256 gray levels.

The method of Paragraph B, wherein the image-taking intervals may be between 0.5 and 1 second, wherein the means for taking and storing digital images may be placed at a distance of approximately 10 cm to 15 cm from the lamp.

The method of Paragraph B, wherein the image-taking intervals may be between 0.5 and 1 second, wherein the means for taking and storing digital images may be placed at a distance of approximately 10 cm to 15 cm from the lamp, wherein the means for taking and storing digital images is set so that the stored digital image contains the image of all the graduated scale of the device for determining the smoke point.

The method of Paragraph B, wherein the number of digital images of each series may be at least equal to 10.

The method of Paragraph B, wherein the method may employs any testing device of Paragraph A or any of the paragraphs with modifications of Paragraph A.

Paragraph C. The invention may also provide a testing device for determining smoke point of a hydrocarbon, comprising:

an apparatus for determining the smoke point conforming to the specifications of an ASTM D1322-19 standard, means for taking a series of digital images of a flame;

an ambient pressure sensor for measuring ambient pressure;

a computer system linked to the means for taking the series of digital images of a flame, linked to the ambient pressure sensor, the computer system programmed to enable digital images taken by the means for taking a series of digital images to be analyzed to measure flame height, and for using pressure measured by the pressure sensor to correct measured flame point values of the hydrocarbon based on ambient pressure measured by the ambient pressure sensor as a function of a difference between a current ambient pressure measured by the pressure sensor during testing and a normalized ambient pressure value.

In the testing device of Paragraph C, the means for taking a series of digital images of a flame may comprise a digital camera;

wherein the apparatus for determining the smoke point conforming to the specifications of an ASTM D1322-19 standard comprises a candle for holding a wick, a graduated scale against which to measure flame height, a gallery configured through which to take the digital images of the flame and the graduated scale, a candle displacement system for adjusting height of a flame from the wick of the candle.

The testing device of Paragraph C, may further comprise:

a power supply, and a housing for containing:

the means for taking a series of digital images of a flame comprising a digital camera, the ambient pressure sensor, and the computer system linked to the means for taking the series of digital images, wherein the computer system comprises electronics comprising a microprocessor.

In the testing device of Paragraph C, the testing device may comprise means for ventilation, an air intake vent for admitting air flow to the test apparatus housing and an air exhaust vent for discharging out of the housing air flow that has been heated within the test apparatus housing.

Paragraph D. The invention may also provide a method of determining smoke point of a hydrocarbon fuel sample, comprising:

measuring ambient pressure with an ambient pressure sensor, testing the fuel sample, said testing comprising:

identifying, among different appearances of a flame according to the position of the burner in a lamp, of a particular appearance of a flame, reading the height of the flame on a graduated scale, using means for taking and storing digital images to take and store a series of digital images of the flame at such intervals that are sufficiently close to enable, by analyzing these digital images, the detection of change in the shape of the flame, measuring height of the flame at the moment of the change of shape of the flame, said height being considered the measured smoke point of the hydrocarbon under test, and inputting the measured height of the flame and measured ambient pressure to a computer system linked to the means for taking and storing digital images and the ambient pressure temperature sensor;

said computer system automatically using ambient pressure measured by the ambient pressure sensor and correcting measured height of the flame values of the hydrocarbon as a function of a difference between a current ambient pressure measured by the pressure sensor during testing and a normalized pressure ambient pressure to calculate a corrected smoke point; and reporting the corrected smoke point.

The method of Paragraph D, may determine the smoke point conforming to the specifications of an ASTM D1322-19 standard.

The method of Paragraph D, wherein the method may employs any testing device of Paragraph C or any of the paragraphs with modifications of Paragraph C.

The method of Paragraph D, wherein the detection of the change in the shape of the flame may be achieved by measuring the sudden change in the speed of reduction of the Feret diameter of the image of the flame.

While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

SAMPLE CALCULATION—RELATIVE
HUMIDITY TO ABSOLUTE HUMIDITY
CONVERSION FORMULA

1. Saturated vapor pressure of water between 16° C. and 30° C., saturated vapor pressure of water can be approximate by the following formula:

$$svP = 4.528945 \times T°C.^2 - 35.685271 \times T°C. + 1235.814887$$

with:
- svP: saturated vapor pressure of water in Pascal (Pa)
- T° C.: Temperature in degrees Celsius (° C.)

2. Partial vapor pressure $$pvP = svP \times \frac{\% RH}{100}$$

with:
- pvP: partial vapor pressure in Pascal (Pa)
- % RH: relative humidity in percent (%)

3. Dry Air density $$d_{dry\ air} = \frac{P_{atm} \times M_{dry\ air}}{R \times T° K}$$

with:
- $d_{dry\ air}$: dry air density in kg/m³
- $P_{Atm}$: atmospheric pressure in Pascal (Pa)
- $M_{dry\ air}$: Molar mass of dry air in kg/mol=0.028965 kg/mol
- R: universal gas constant in J/(K·mol)=8,3144621 J/(K·mol)
- T° K: Temperature in Kelvin (K)

4. Absolute humidity $$x = 0.622 \times \frac{pvP}{P_{Atm} - pvP}$$

with:
- x: absolute humidity in $kg_{water}/kg_{dry\ air}$
- pvP: partial vapor pressure in Pascal (Pa)
- $P_{Atm}$: atmospheric pressure in Pascal (Pa)

$$AH = x \times d_{dry\ air}$$

with
- AH: absolute humidity in $kg_{water}/m^3_{air}$
- x: absolute humidity in $kg_{water}/kg_{dry\ air}$
- $d_{dry\ air}$: dry air density in kg/m³

5. General conversion formula $$AH = 0.622 \times \frac{(4.528945 \times T°C.^2 - 35.685271 \times T°C. + 1235.814887) \times \frac{\% RH}{100}}{P_{Atm} - \left((4.528945 \times T°C.^2 - 3.685271 \times T°C. + 1235.814887 \times \frac{\% RH}{100})\right)} \times \frac{P_{atm} \times M_{dry\ air}}{R \times T° K}$$

with:
- AH: absolute humidity in $k_{water}/m^3_{air}$
- T° C.: Temperature in degrees Celsius (° C.)
- % RH: relative humidity in percent (%)
- $d_{dry\ air}$: dry air density in kg/m³
- $P_{Atm}$: atmospheric pressure in Pascal (Pa)
- $M_{dry\ air}$: Molar mass of dry air in kg/mol=0.028965 kg/mol
- R: universal gas constant in J/(K·mol)=8.3144621 J/(K·mol)
- T° K: Temperature in Kelvin (K)

6. Application test lab environment:
- relative humidity: RH=40%
- temperature: T° C.=22° C.
- Atmospheric pressure: $P_{atm}$=1013 hPa $$AH = 0.622 \times \frac{(4.528945 \times 22^2 - 35.685271 \times 22 + 1235.814887) \times \frac{40}{100}}{101300 - \left((4.528945 \times 22^2 - 35.685271 \times 22 + 1235.814887) \times \frac{40}{100}\right)} \times \frac{101300 \times 0.028965}{8,3144621 \times (22 + 273.15)}$$

$$AH = 0.00784\ kg/m^3$$

What is claimed is:

1. A testing device for determining smoke point of a hydrocarbon, comprising:
   an apparatus for determining the smoke point conforming to the specifications of an ASTM D1322-19 standard;
   an imaging device for taking a series of digital images of a flame;
   an ambient relative humidity sensor for measuring relative humidity;
   an ambient temperature sensor for measuring temperature; and
   a computer system linked to the the imaging device for taking the series of digital images of a flame, linked to the ambient relative humidity sensor, and linked to the ambient temperature sensor, the computer system programmed to enable digital images taken by the imaging device to be analyzed to measure flame height, and for using temperature measured by the ambient temperature sensor in combination with relative humidity measured by the ambient relative humidity sensor to calculate an absolute humidity value and to correct the measured flame height as a function of a difference between the calculated absolute humidity value and a normalized absolute humidity value.

2. The testing device of claim 1, further comprising an ambient pressure sensor linked to the computer system, wherein the computer system corrects the measured flame height of the hydrocarbon based on ambient pressure measured by the ambient pressure sensor as a function of a difference between a current ambient pressure measured by the ambient pressure sensor during testing and a normalized pressure value.

3. The testing device of claim 1, wherein the ambient temperature sensor is part of the ambient relative humidity sensor or a separate from the ambient relative humidity sensor.

4. The testing device of claim 3, further comprising a housing having an intake vent and an exhaust vent, wherein the ambient relative humidity sensor is provided proximate to the intake vent.

5. The testing device of claim 4, wherein the housing has an intake vent and an exhaust vent, wherein the ambient temperature sensor is provided proximate to the intake vent.

6. The testing device of claim 1, wherein the normalized absolute humidity value is a value in a range of 0 gr/m$^3$ to 40 gr/m$^3$.

7. A method of determining smoke point of a hydrocarbon fuel sample, comprising:
measuring ambient relative humidity with an ambient relative humidity sensor,
measuring ambient temperature with an ambient temperature sensor,
testing the fuel sample, said testing comprising
using an imaging device for taking and storing digital images to take and store a series of digital images of the flame at such intervals that are sufficiently close to enable, by analyzing these digital images, the detection of change in the shape of the flame, and
identifying, among different appearances of a flame according to the position of the burner in a lamp, of a particular appearance of a flame, and
measuring height of the flame at a moment of the change of shape of the flame, said height being considered measured smoke point of the hydrocarbon under test,
inputting the measured height of the flame and measured ambient relative humidity, and measured ambient temperature to a computer system linked to the imaging device and the ambient relative humidity sensor, and the ambient temperature sensor;
said computer system linked to the imaging device, linked to the humidity sensor, and linked to the temperature sensor, the computer system analyzing digital images taken by the imaging device to measure flame height, and using temperature measured by the ambient temperature sensor in combination with relative humidity measured by the relative humidity sensor to calculate the absolute humidity and to correct the measured flame height as a function of a difference between the calculated absolute humidity and a normalized absolute humidity value to calculate a corrected smoke point; and
reporting the corrected smoke point.

8. The method of claim 7, further comprising measuring ambient pressure with an ambient pressure sensor linked to the computer system, wherein the computer system corrects the measured flame height of the hydrocarbon based on ambient pressure measured by the ambient pressure sensor as a function of a difference between a current ambient pressure measured by the ambient pressure sensor during testing and a normalized pressure ambient pressure value.

9. The method of claim 7, wherein automatically correcting measured flame height comprises correcting calibration values during calibration of the testing apparatus as a function of a difference between current atmospheric pressure measured by the ambient pressure sensor and a normalized standard value.

10. The method of claim 9, wherein the normalized standard value is 101.3 kPa.

11. The method of claim 7, wherein the imaging device for taking and storing digital images comprises a digital camera, wherein automatically correcting measured smoke point comprises normalizing in real time flame point measurements made by the digital camera to a standard pressure.

12. A testing device for determining smoke point of a hydrocarbon, comprising:
an apparatus for determining the smoke point conforming to the specifications of an ASTM D1322-19 standard;
an imaging device for taking a series of digital images of a flame;
an ambient pressure sensor for measuring ambient pressure; and
a computer system linked to the imaging device for taking the series of digital images of a flame, linked to the ambient pressure sensor, the computer system programmed to enable digital images taken by the imaging device for taking a series of digital images to be analyzed to measure flame height, and for using pressure measured by the ambient pressure sensor to correct measured flame height of the hydrocarbon as a function of a difference between a current ambient pressure measured by the ambient pressure sensor during testing and a normalized ambient pressure value.

13. A method of determining smoke point of a hydrocarbon fuel sample, comprising:
measuring ambient pressure with an ambient pressure sensor,
testing the fuel sample, said testing comprising:
identifying, among different appearances of a flame according to the position of the burner in a lamp, of a particular appearance of a flame,
using an imaging device for taking and storing digital images to take and store a series of digital images of the flame at such intervals that are sufficiently close to enable, by analyzing these digital images, the detection of change in the shape of the flame,
measuring height of the flame at the moment of the change of shape of the flame, said height being considered a measured smoke point of the hydrocarbon under test, and
inputting the measured height of the flame and measured ambient pressure to a computer system linked to the imaging device for taking and storing digital images and the ambient pressure temperature sensor;
said computer system automatically using ambient pressure measured by the ambient pressure sensor and correcting measured height of the flame values of the hydrocarbon as a function of a difference between a current ambient pressure measured by the ambient pressure sensor during testing and a normalized ambient pressure to calculate a corrected smoke point; and
reporting the corrected smoke point.

* * * * *

UNITED STATES PATENT AND TRADEMARK OFFICE
CERTIFICATE OF CORRECTION

| | |
|---|---|
| PATENT NO. | : 11,609,197 B2 |
| APPLICATION NO. | : 17/343251 |
| DATED | : March 21, 2023 |
| INVENTOR(S) | : Martial Lépinay and Jean Christien |

It is certified that error appears in the above-identified patent and that said Letters Patent is hereby corrected as shown below:

In the Claims

Claim 1, Column 34, Line 36, reading:
"a computer system linked to the the imaging device for"

Should be changed to:
-- a computer system linked to the imaging device for --

Signed and Sealed this
Thirtieth Day of May, 2023

Katherine Kelly Vidal
*Director of the United States Patent and Trademark Office*